(12) United States Patent
Milne et al.

(10) Patent No.: US 9,150,504 B2
(45) Date of Patent: Oct. 6, 2015

(54) FATTY ACID GUANIDINE AND SALICYLATE GUANIDINE DERIVATIVES AND THEIR USES

(75) Inventors: Jill C. Milne, Brookline, MA (US); Michael R. Jirousek, Cambridge, MA (US); Jean E. Bemis, Arlington, MA (US); Chi B. Vu, Arlington, MA (US); Amal Ting, Newton, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 368 days.

(21) Appl. No.: 13/458,494

(22) Filed: Apr. 27, 2012

(65) Prior Publication Data

US 2012/0277305 A1    Nov. 1, 2012

Related U.S. Application Data

(60) Provisional application No. 61/512,686, filed on Jul. 28, 2011, provisional application No. 61/480,773, filed on Apr. 29, 2011.

(51) Int. Cl.
*C07C 279/26* (2006.01)
*C07C 279/14* (2006.01)

(52) U.S. Cl.
CPC ............. *C07C 279/26* (2013.01); *C07C 279/14* (2013.01)

(58) Field of Classification Search
None
See application file for complete search history.

(56) References Cited

U.S. PATENT DOCUMENTS

| 6,075,031 | A | 6/2000 | Kaddurah-Daouk et al. | |
|---|---|---|---|---|
| 7,511,163 | B2 * | 3/2009 | Chaudhuri et al. | 554/152 |
| 2004/0106589 | A1 * | 6/2004 | Webb et al. | 514/182 |
| 2004/0228884 | A1 * | 11/2004 | Gupta | 424/401 |
| 2008/0188457 | A1 * | 8/2008 | Barlow et al. | 514/212.06 |
| 2010/0104589 | A1 * | 4/2010 | Govindan et al. | 424/181.1 |

FOREIGN PATENT DOCUMENTS

| DE | 246029 | * | 8/1987 | ............ A61K 47/00 |
|---|---|---|---|---|
| WO | WO2008/101309 | * | 8/2008 | ............ C07C 279/14 |
| WO | WO2008/101310 | * | 8/2008 | ............ C07C 279/22 |
| WO | WO2009/076741 | * | 6/2009 | ............ C07C 279/08 |
| WO | WO 2010/108583 | * | 9/2010 | ............ C07D 251/10 |

OTHER PUBLICATIONS

Wacharine-Antar, S., et al., Resolution of (+)-Imeglimin-s,4-dichlorophenylacetate Methanol Solvate by Preferential Crystallization, 2010, Organic Process Research & Development, vol. 14, No. 6, pp. 1358-1363.*
Altmassn, H., et al., Improving bio-availability of ionogenic medicaments e.g. buformin using a carrier contg. an alky-substituted salicylic acid., 1987, DD 246026, English Translation, abstract, 3 pages.*
International Search Report for International Application No. PCT/US12/35497, mailed Jul. 27, 2012, 2 pages.
Written Opinion for International Application No. PCT/US12/35497, mailed Jul. 27, 2012, 7 pages.

* cited by examiner

*Primary Examiner* — Yate K Cutliff
(74) *Attorney, Agent, or Firm* — Goodwin Procter LLP

(57) ABSTRACT

The invention relates to fatty acid guanidine or salicylate guanidine derivatives; compositions comprising an effective amount of a fatty acid guanidine or salicylate guanidine derivative; and methods for treating or preventing a metabolic disease comprising the administration of an effective amount of a fatty acid guanidine or salicylate guanidine derivative.

18 Claims, No Drawings

FATTY ACID GUANIDINE AND SALICYLATE GUANIDINE DERIVATIVES AND THEIR USES

CROSS-REFERENCE TO RELATED APPLICATIONS

This application claims priority to and the benefit of U.S. Provisional Application Ser. No. 61/512,686, filed Jul. 28, 2011 and entitled "Conjugates of Guanidine Derivatives and Their Uses," and U.S. Provisional Application No. 61/480,773, filed Apr. 29, 2011 and entitled "Fatty Acid Metformin Derivatives and Their Uses," the disclosures of both of which are hereby incorporated by reference in their entirety.

FIELD OF THE INVENTION

The invention relates to fatty acid guanidine derivatives and salicylate guanidine derivatives; compositions comprising an effective amount of a fatty acid guanidine derivative or salicylate guanidine derivative; and methods for treating or preventing a metabolic disease comprising the administration of an effective amount of a fatty acid guanidine derivative or salicylate guanidine derivative. All patents, patent applications, and publications cited herein are hereby incorporated by reference in their entireties.

BACKGROUND OF THE INVENTION

Oily cold water fish, such as salmon, trout, herring, and tuna are the source of dietary marine omega-3 fatty acids, with eicosapentaenoic acid (EPA) and docosahexaenoic acid (DHA) being the key marine derived omega-3 fatty acids. Omega-3 fatty acids have previously been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been shown to improve in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as dietary supplements part of therapy used to treat dyslipidemia, and anti-inflammatory properties. A higher intake of omega-3 fatty acids lower levels of circulating TNF-α and IL-6, two of the cytokines that are markedly increased during inflammation processes (Chapkin et al, *Prostaglandins, Leukot Essent Fatty Acids* 2009, 81, p. 187-191; Duda et al, *Cardiovasc Res* 2009, 84, p. 33-41). In addition, a higher intake of omega-3 fatty acids has also been shown to increase levels of the well-characterized anti-inflammatory cytokine IL-10 (Bradley et al, *Obesity (Silver Spring)* 2008, 16, p. 938-944). More recently, there is additional evidence that omega-3 fatty acids could play a significant role in oncology (Anderson et al, *Lipids in Health and Disease* 2009, 8, p. 33; Bougnoux et al, *Progress in Lipid Research* 2010, 49, p. 76-86; Erickson et al, *Prostaglandins, Leukotrienes and Essential Fatty Acids* 2010, 82, p. 237-241). In a study using the xenograft model in nude mice, treatment with omega-3 fatty acids, such as DHA and EPA, resulted in breast tumor regression. Here, treatment with DHA/EPA appeared to increase the level of PTEN protein and attenuate the PI 3 kinase and Akt kinase activity as well as the expression of the anti-apoptotic proteins Bcl-2 and Bcl-XL in the breast tumors (Ghosh-Choudhury, T. et al. *Breast Cancer Res. Treat.* 2009, 118 (1), 213-228). Additional evidence supporting the use of omega-3 fatty acids in oncology also appeared in a recent study by Lim et al. showing that DHA/EPA could inhibit hepatocellular carcinoma cell growth, presumably by blocking β-catenin and cyclooxygenase-2 (Lim, K. et al. *Mol. Cancer Ther.* 2009, 8 (11), 3046-3055).

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42).

Metformin has long been the standard of care treatment for patients with Type 2 Diabetes. It has shown to be anti-atherosclerotic, cardioprotective, has positive effects on vascular endothelium, and suppressant effects on glycation, oxidative stress and in the formation of adhesion molecules. In addition, metformin has shown favorable effects on lipid profiles, reduces liver volume, improves hepatic insulin sensitivity and has positive effects on polycystic ovary syndrome. (Scarpello, J H and Howlett, H C, *Diab Vasc Dis Res,* 2008, 5(3), 157-167, Nestler, J., *New England Journal of Medicine,* 2008, 358, p. 47-54). Metformin acts upon the NF-kB axis by increasing the antiangiogenic Thrombospondin-1 (Randeva, H. et al, *Cardiovascular Research,* 2009, 83, 566-574) as well as by inhibiting P-glycoprotein expression (Jeong, H G e al, *British J Pharmacology,* 2011, 162(5), 1096-1108). Other guanidine derivatives that have been shown to have anti-diabetic activity include N-methyl-N-guanylglycine, also referred to as creatine. In a comparison study regarding the anti-hyperglycemic effects of creatine (2×3 g a day) and metformin (2×500 mg a day) in recently detected type 2 diabetics, both agents have been shown to elicit similar glucose lowering effects (Rocic et al, *Clinical and Investigative Medicine* 2009, issue 6, p. E322-E326). Metformin has been used widely since its introduction in the mid 1990's. However, because of its fully protonated form under physiological conditions, it is slowly and incompletely absorbed from the upper intestine upon oral administration. Furthermore, metformin displays some uncomfortable gastrointestinal side effects which sometimes limit patient compliance and effectiveness. Hence, a number of different pro-drug forms of metformin have been investigated. Some of these are detailed in Huttunen et al, *Synthesis* 2008, p. 3619-3624. Some of these pro-drug forms included carbamate derivatives and rigid phenyl derivatives that allowed 1,6-elimination of either a p-amino or p-hydroxybenzylic group. Other cyclic derivatives of metformin have also been prepared in order to improve its tolerability. These cyclic derivatives of metformin included imeglimin (Wacharine-Antar et al, *Org. Process Research & Development* 2010, 14, p. 1358-2363) and other compounds disclosed in Helmreich et al's WO 2010108583.

Salicylates and other non-steroidal anti-inflammatory drugs (NSAIDs) can influence the NF-κB pathway, allowing people to derive relief and reduced inflammation from these drugs. Aspirin and COX inhibitors act to reduce inflammation by reversibly or irreversibly blocking access to the hydrophobic channel via acetylation of serine 530 (COX-1) or Serine 516 (COX-2). For some selective NSAIDs with a carboxylate group, there is significant charge-charge interaction with Arginine 120. This binding or interaction blocks the cyclooxygenase enzyme that forms $PGH_2$. Salicylate does not irreversibly inhibit cyclooxygenase because it lacks the ability to acylate the COX enzyme and has little, if any, direct inhibitory action on the COX enzyme at concentrations that are relevant in vivo. Salicylate has been shown to inhibit the activity of IKKβ and thereby inhibit NFκB leading to reduced expression of COX-2 in an inflammatory state where COX-2 expression has been induced.

Because of the ability of guanidine derivatives such as, for example, metformin and omega-3 fatty acid or salicylic acid to act on the NF-κB axis, a synergistic activity would provide a great benefit in treating multiple myeloma, myelodysplastic syndromes (MDS) or other metabolic diseases.

SUMMARY OF THE INVENTION

The invention is based in part on the discovery of fatty acid guanidine derivatives or salicylate guanidine derivatives and their demonstrated effects in achieving improved treatment that cannot be achieved by administering salicylate or fatty acids or guanidine derivatives alone or in combination. The fatty acid guanidine derivatives or salicylate guanidine derivatives are designed to be stable in the plasma. In target tissues, the individual components (i.e. fatty acid, guanidine derivative or salicylic acid) are then released by the action of various intracellular enzymes. These novel fatty acid guanidine derivatives or salicylate guanidine derivatives are useful in the treatment or prevention of metabolic diseases including diabetic nephropathy, chronic kidney disease (CKD), atherosclerosis, dyslipidemia, coronary heart disease, hypercholesterolemia, Type 2 diabetes, elevated cholesterol, metabolic syndrome, polycystic ovary syndrome and cardiovascular disease. In addition, they are useful in the treatment of autoimmune diseases such as rheumatoid arthritis, cystic fibrosis, inflammatory bowel diseases (including colitis and Crohn's disease).

Accordingly in one aspect, a molecular conjugate is described which comprises a guanidine derivative covalently linked to either salicylic acid or a fatty acid, wherein the fatty acid is selected from the group consisting of omega-3 fatty acids and fatty acids that are metabolized in vivo to omega-3 fatty acids, and the conjugate is capable of hydrolysis to produce a free guanidine and free salicylic acid or fatty acid.

In another aspect, compounds of the Formula I are described:

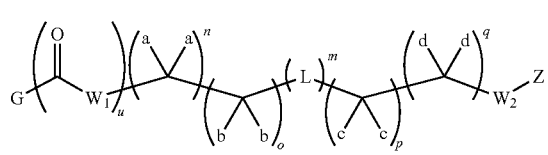

Formula I and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

G is independently

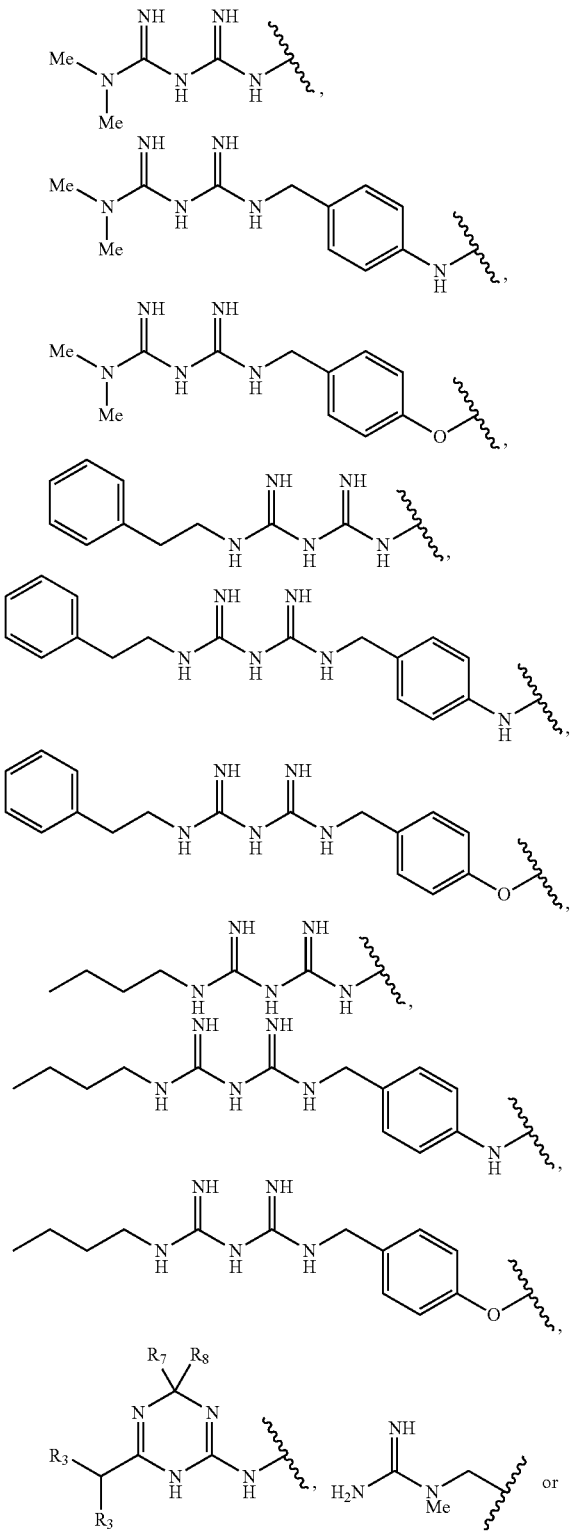

-continued
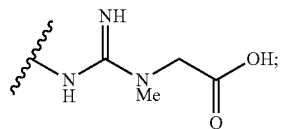
each a, b, c, and d is independently —H, -D, —CH₃, —OCH₃, —OCH₂CH₃, —C(O)OR, —O—Z, or benzyl, or two of a, b, c, and d can be taken together, along with the single carbon to which they are bound, to form a cycloalkyl or heterocycle;
each n, o, p, and q is independently 0, 1 or 2;
L is independently null, —O—, —S—, —S(O)—, —S(O)₂—, —S—S—, —(C₁-C₆alkyl)-, —(C₃-C₆cycloalkyl)-, a heterocycle, a heteroaryl,
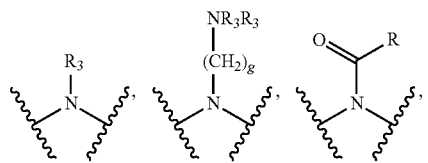
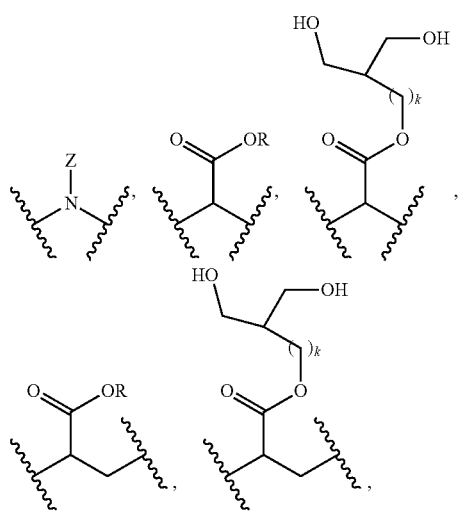
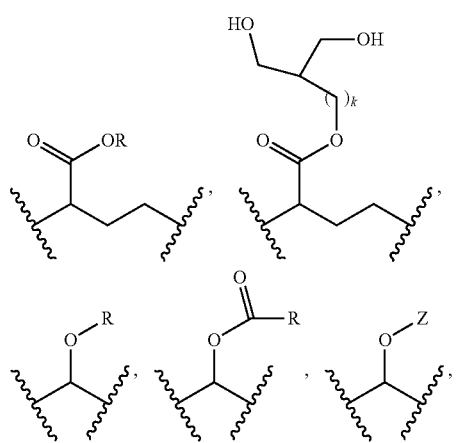
-continued
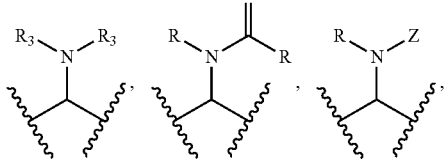
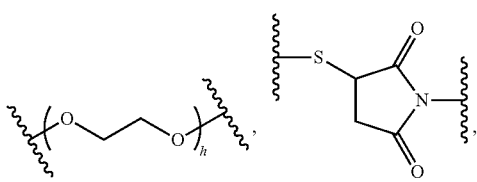
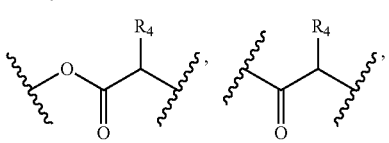
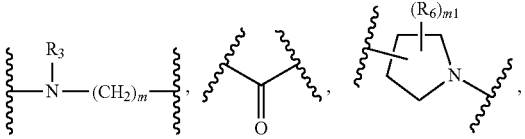
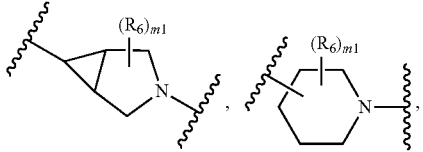
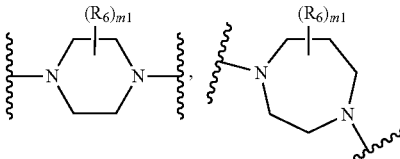
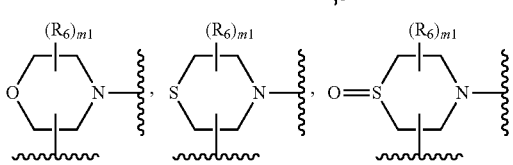
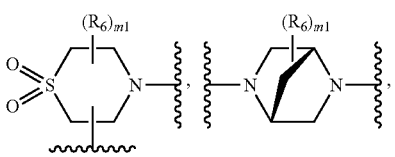
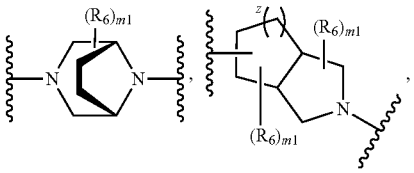
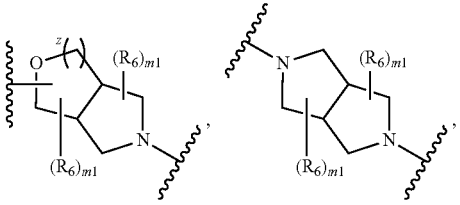

-continued

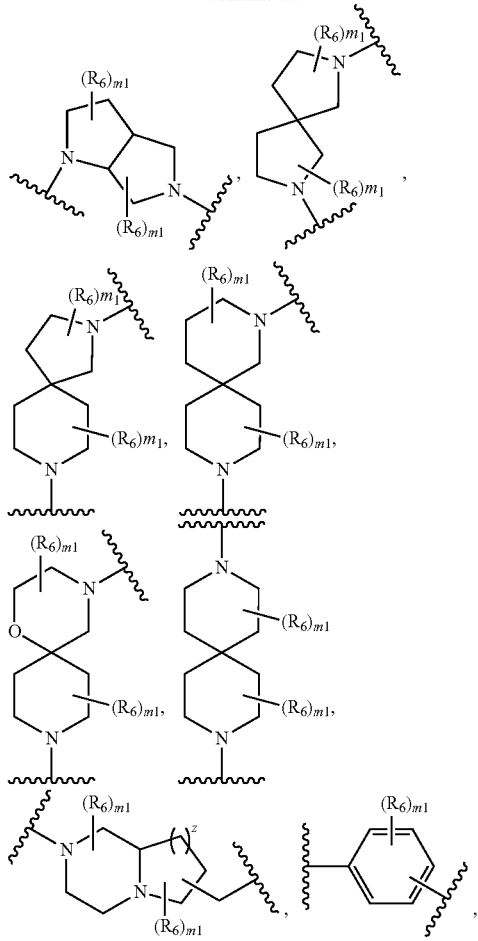

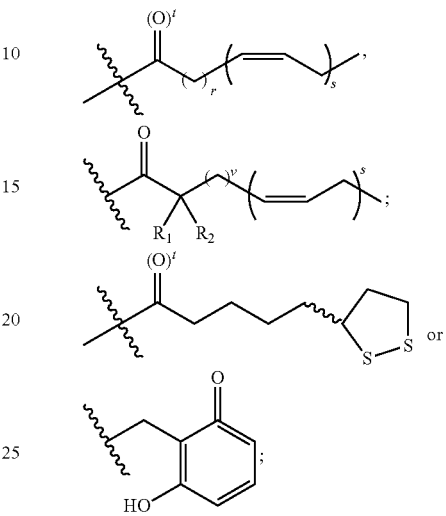

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

$R_7$ and $R_8$ are independently H, $C_1$-$C_6$ alkyl, trifluoromethyl, a cycloalkyl, a heterocycle, or $R_7$ and $R_8$ can be taken together to form a 3-8 membered ring that can optionally contain one or more heteroatom chosen from N, O and S.

each g is independently 2, 3 or 4;
each h is independently 1, 2, 3 or 4;
m is 0, 1, 2, 3, 4 or 5; if m is more than 1, then L can be the same or different;
m1 is 0, 1, 2 or 3;
k is 0, 1, 2, or 3;
u is 0 or 1;
z is 1, 2, or 3;
each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each Z is independently —H,

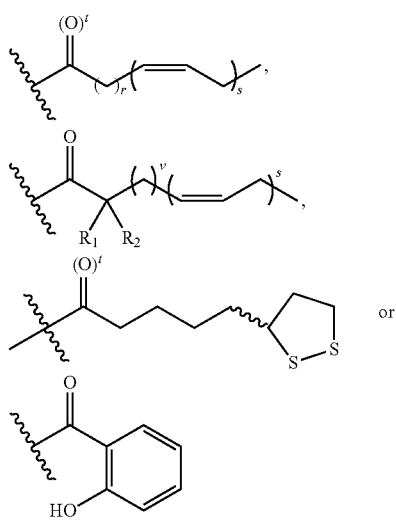

with the proviso that there is at least one of

[additional structures shown]

in the compound;
each r is independently 2, 3, or 7;
each s is independently 3, 5, or 6;
each t is independently 0 or 1;
each v is independently 1, 2, or 6;
$R_1$ and $R_2$ are independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
each R is independently —H, —$C_1$-$C_3$ alkyl, or straight or branched $C_1$-$C_4$ alkyl optionally substituted with OH, or halogen.

In another aspect, compounds of the Formula Ia are described:

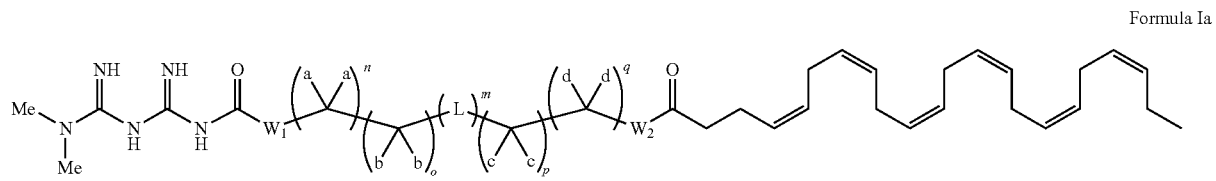

Formula Ia and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1 or 2;

L is independently null, —O—, —S—, —S(O)—, —S(O)$_2$—, —S—S—, —($C_1$-$C_6$alkyl)-, —($C_3$-$C_6$cycloalkyl)-, a heterocycle, a heteroaryl,

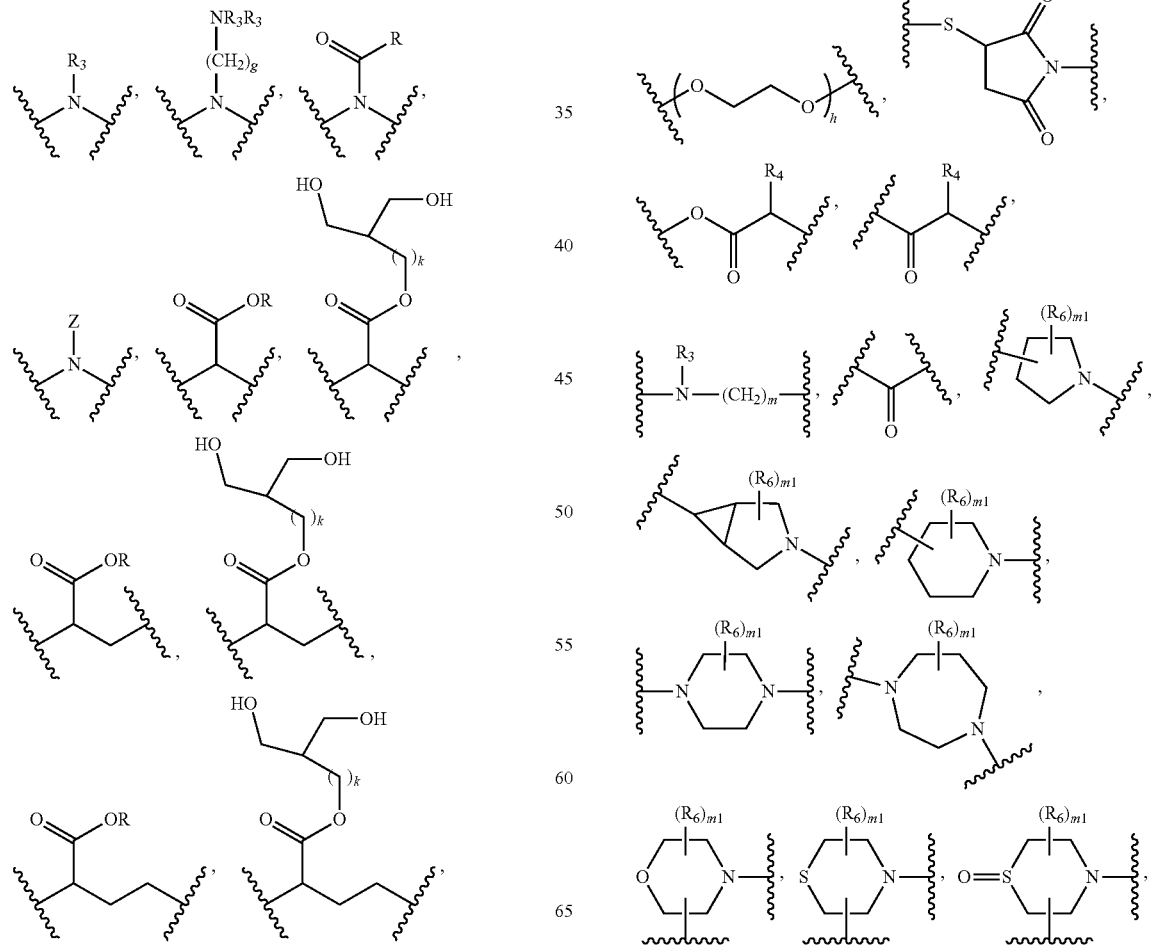

-continued

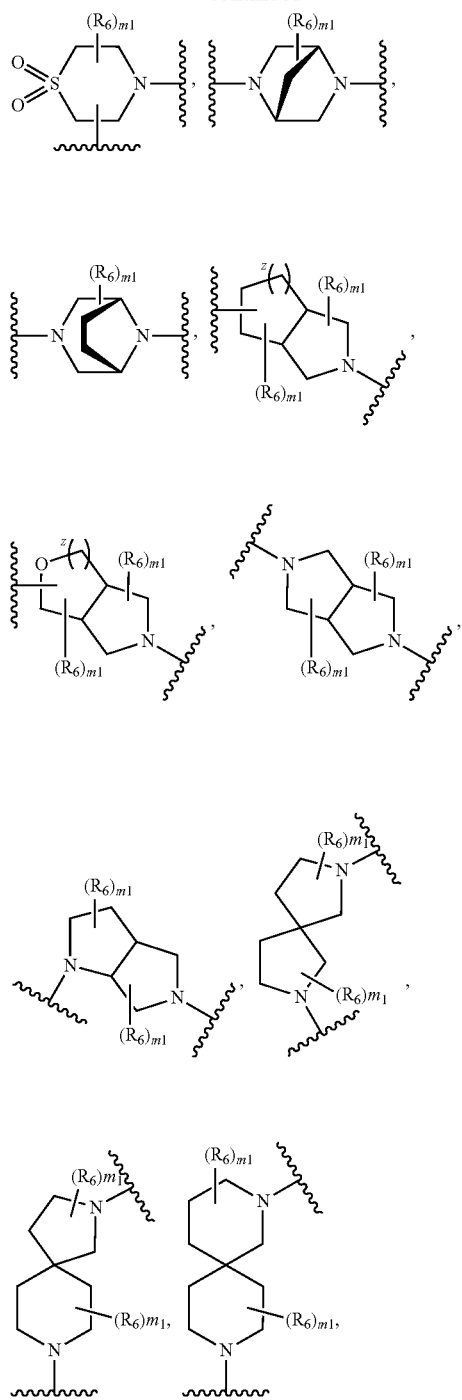

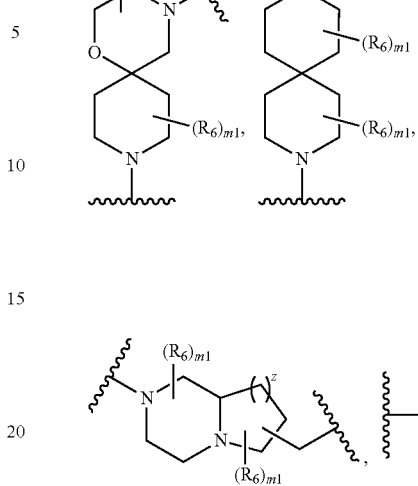

wherein the representation of L is not limited directionally left to right as is depicted, rather either the left side or the right side of L can be bound to the $W_1$ side of the compound of Formula Ia;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;
each h is independently 1, 2, 3 or 4;
m is 0, 1, 2, 3, 4 or 5; if m is more than 1, then L can be the same or different;
m1 is 0, 1, 2 or 3;
k is 0, 1, 2, or 3;
z is 1, 2, or 3;

each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids; and each R is independently —H, —$C_1$-$C_3$ alkyl, or straight or branched $C_1$-$C_4$ alkyl optionally substituted with OH, or halogen;

In another aspect, compounds of the Formula Ib are described:

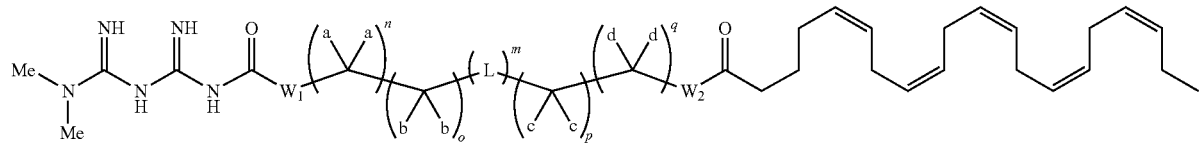

Formula Ib and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

each a, b, c, and d is independently —H, -D, —CH$_3$, —OCH$_3$, —OCH$_2$CH$_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1 or 2;

L is independently null, —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,

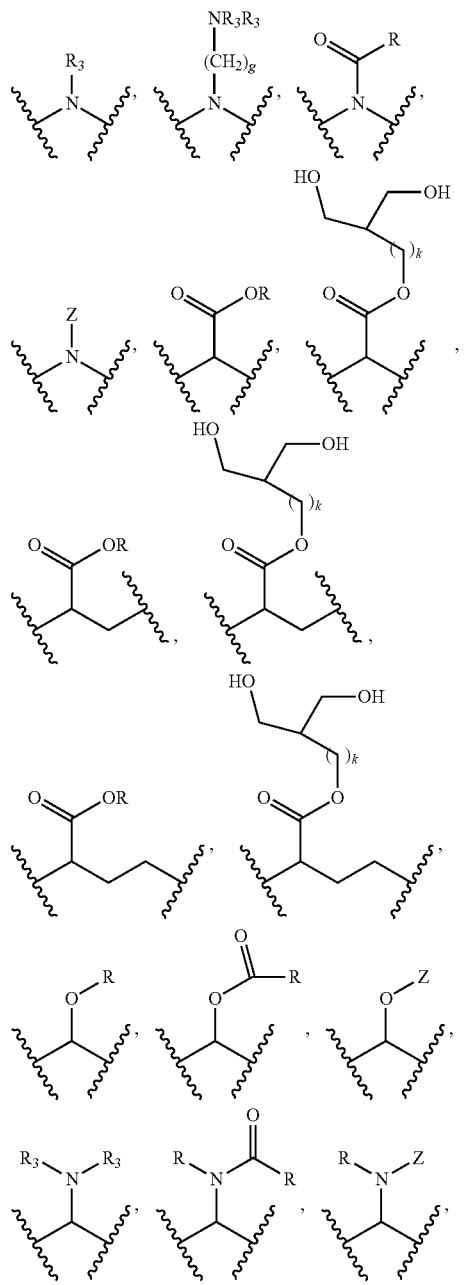

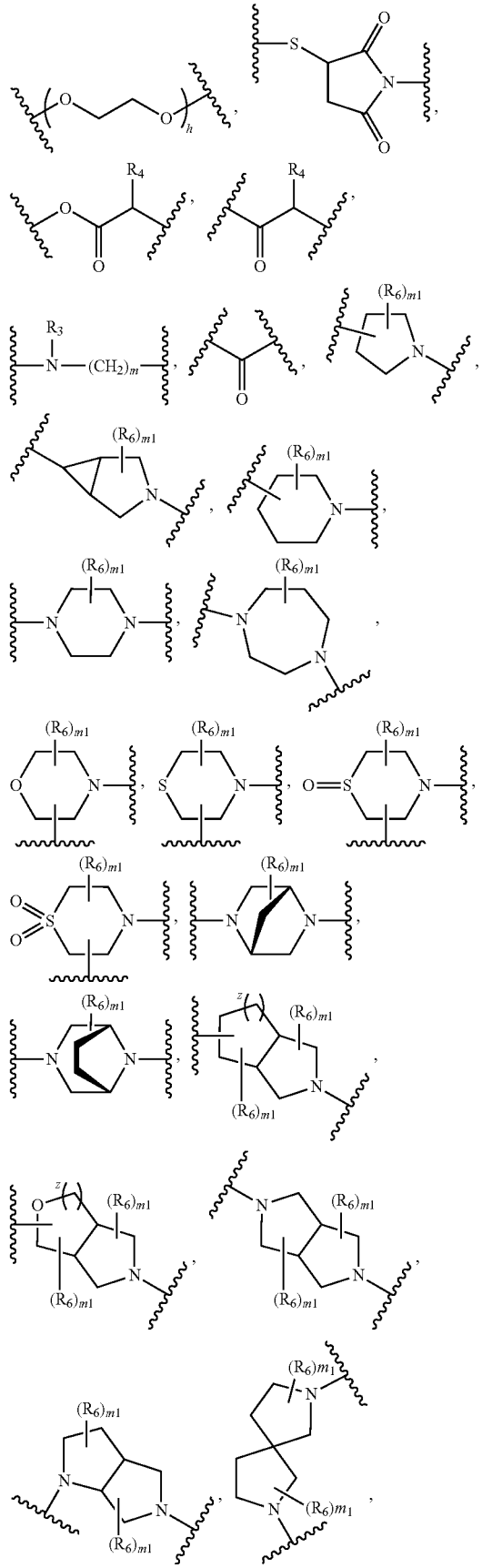

-continued

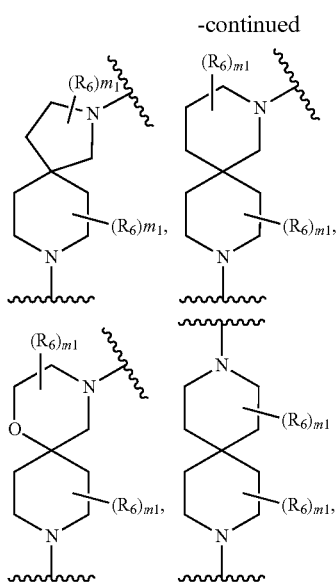

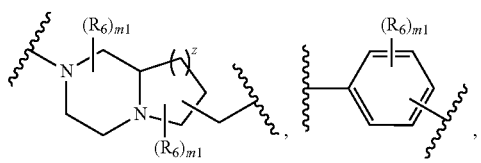

wherein the representation of L is not limited directionally left to right as is depicted, rather either the left side or the right side of L can be bound to the $W_1$ side of the compound of Formula Ib;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;

each h is independently 1, 2, 3 or 4;

m is 0, 1, 2, 3, 4 or 5; if m is more than 1, then L can be the same or different;

m1 is 0, 1, 2 or 3;

k is 0, 1, 2, or 3;

z is 1, 2, or 3;

each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids; and each R is independently —H, —$C_1$-$C_3$ alkyl, or straight or branched $C_1$-$C_4$ alkyl optionally substituted with OH, or halogen;

In another aspect, compounds of the Formula Ic are described:

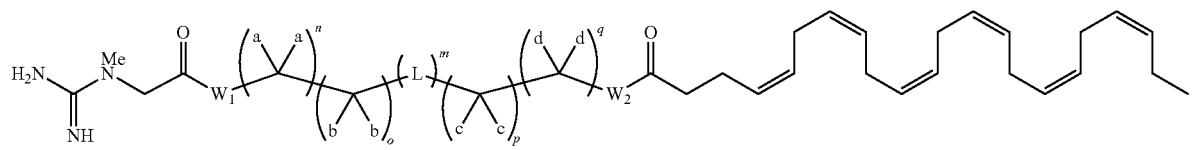

Formula Ic and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1 or 2;

L is independently null, —O—, —S—, —S(O)—, —S(O)$_2$—, —S—S—, —($C_1$-$C_6$alkyl)-, —($C_3$-$C_6$cycloalkyl)-, a heterocycle, a heteroaryl,

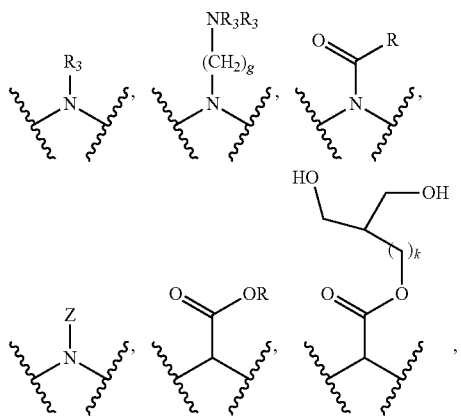

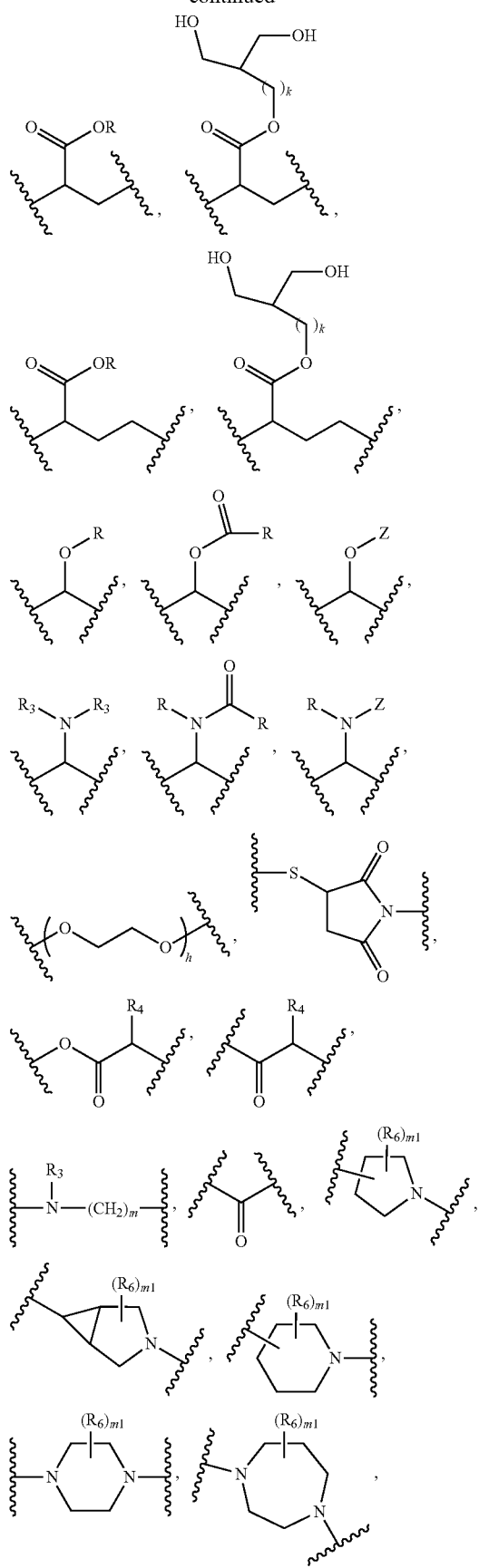
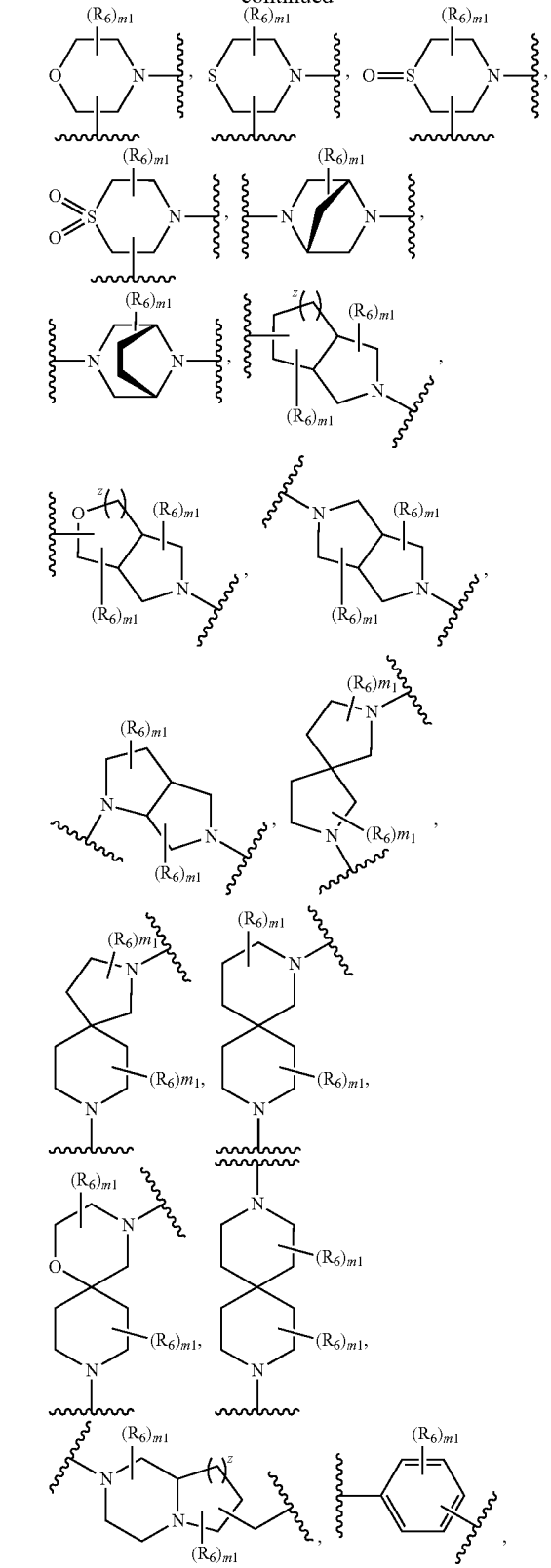
wherein the representation of L is not limited directionally left to right as is depicted, rather either the left side or the right side of L can be bound to the $W_1$ side of the compound of Formula Ic;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NHC(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;

each g is independently 2, 3 or 4;
each h is independently 1, 2, 3 or 4;
m is 0, 1, 2, 3, 4 or 5; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;
each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids; and
each R is independently —H, —$C_1$-$C_3$ alkyl, or straight or branched $C_1$-$C_4$ alkyl optionally substituted with OH, or halogen;

In another aspect, compounds of the Formula Id are described:

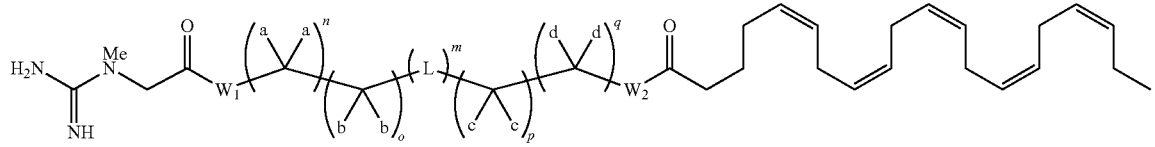

Formula Id and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1 or 2;

L is independently null, —O—, —S—, —S(O)—, —S(O)$_2$—, —S—S—, —($C_1$-$C_6$alkyl)-, —($C_3$-$C_6$cycloalkyl)-, a heterocycle, a heteroaryl,

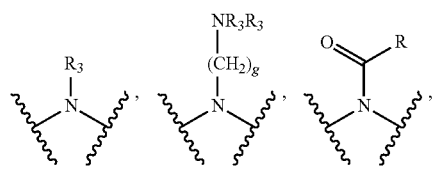

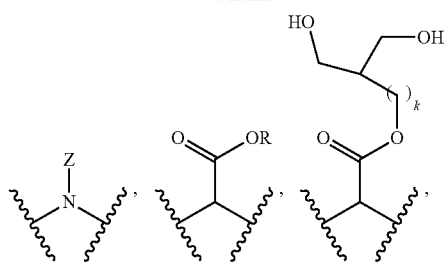

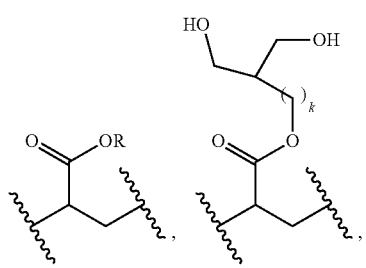

-continued

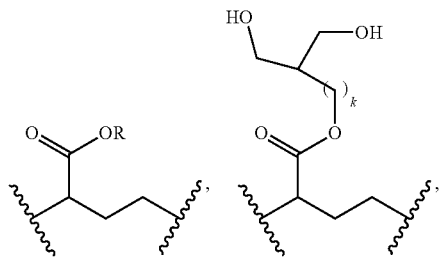

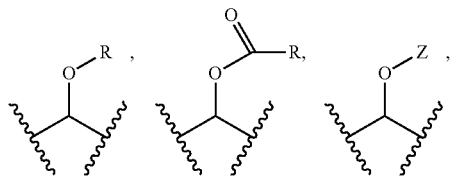

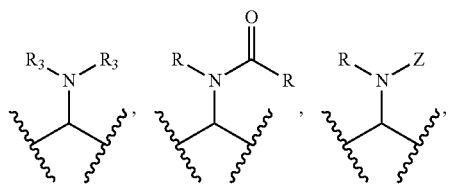

-continued

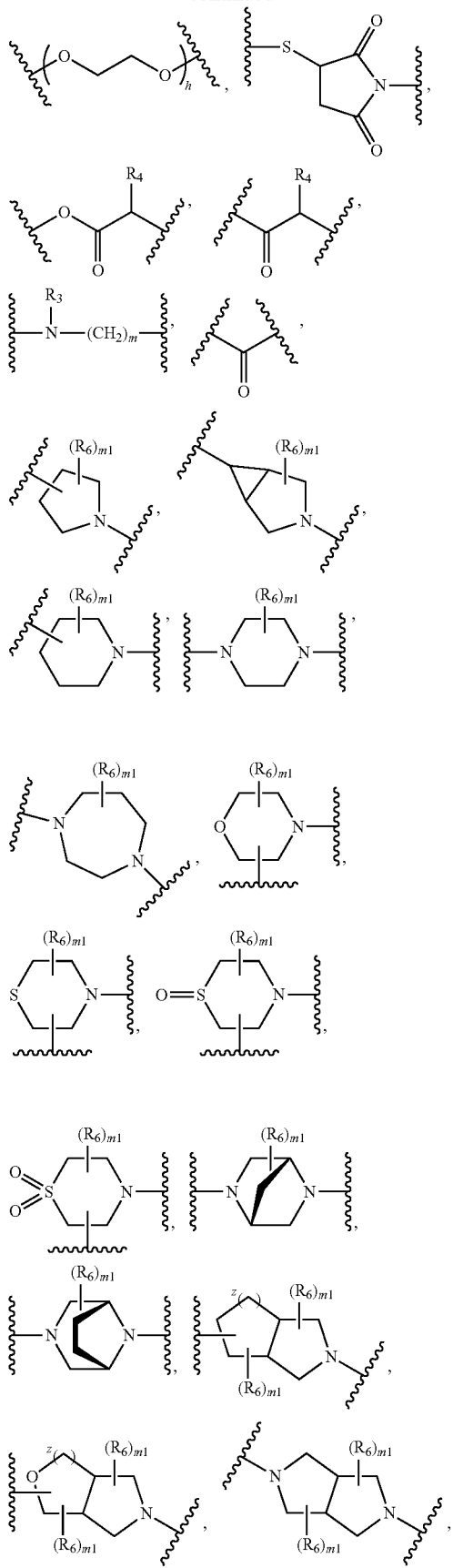

-continued

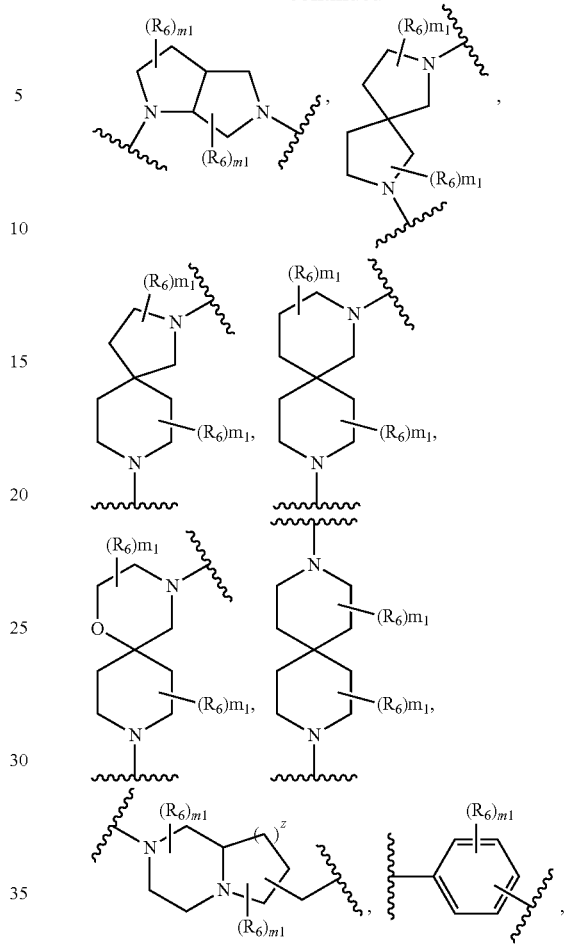

wherein the representation of L is not limited directionally left to right as is depicted, rather either the left side or the right side of L can be bound to the $W_1$ side of the compound of Formula Id;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;

each h is independently 1, 2, 3 or 4;

m is 0, 1, 2, 3, 4 or 5; if m is more than 1, then L can be the same or different;

m1 is 0, 1, 2 or 3;

k is 0, 1, 2, or 3;

z is 1, 2, or 3;

each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids; and each R is independently —H, —$C_1$-$C_3$ alkyl, or straight or branched $C_1$-$C_4$ alkyl optionally substituted with OH, or halogen;

In Formula I, Ia, Ib, Ic and Id any one or more of H may be substituted with a deuterium. It is also understood in Formula I, Ia, Ib, Ic and Id that a methyl substituent can be substituted with a $C_1$-$C_6$ alkyl.

Also described are pharmaceutical formulations comprising at least one fatty acid guanidine derivative or salicylate guanidine derivative.

Also described herein are methods of treating a disease susceptible to treatment with a fatty acid guanidine derivative or salicylate guanidine derivative in a patient in need thereof by administering to the patient an effective amount of a fatty acid guanidine derivative or salicylate guanidine derivative.

Also described herein are methods of treating metabolic diseases by administering to a patient in need thereof an effective amount of a fatty acid guanidine derivative or salicylate guanidine derivative.

The invention also includes pharmaceutical compositions that comprise an effective amount of a fatty acid guanidine derivative or salicylate guanidine derivative and a pharmaceutically acceptable carrier. The compositions are useful for treatment or prevention of metabolic diseases including diabetic nephropathy, chronic kidney disease (CKD), atherosclerosis, dyslipidemia, coronary heart disease, hypercholesterimia, Type 2 diabetes, elevated cholesterol, metabolic syndrome and cardiovascular disease. In addition, they are useful in the treatment of autoimmune diseases such as rheumatoid arthritis, cystic fibrosis, inflammatory bowel diseases (including colitis and Crohn's disease). The invention includes a fatty acid guanidine derivative or salicylate guanidine derivative provided as a pharmaceutically acceptable prodrug, a hydrate, a salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

The fatty acid guanidine derivative or salicylate guanidine derivative derivatives have been designed to bring together guanidine derivatives and omega-3 fatty acids or guanidine and salicylate into a single molecular conjugate. The activity of the fatty acid guanidine derivative or salicylate guanidine derivative is substantially greater than the sum of the individual components of the molecular conjugate, suggesting that the activity induced by the fatty acid guanidine derivative or salicylate guanidine derivative derivatives is synergistic.

DEFINITIONS

The following definitions are used in connection with the fatty acid guanidine derivative or salicylate guanidine derivative:

The term "fatty acid guanidine derivative or salicylate guanidine derivative" includes any and all possible isomers, stereoisomers, enantiomers, diastereomers, tautomers, pharmaceutically acceptable salts, hydrates, solvates, and prodrugs of the fatty acid metformin derivatives described herein.

The term salicylate includes salicylic acid or derivatives of salicylic acid such as 5-amino salicylic, diflunisal and triflusal.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on an alkyl or cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a monocyclic or bicyclic ring structure having 5 to 12 ring atoms wherein one or more of the ring atoms is a heteroatom, e.g. N, O or S and wherein one or more rings of the bicyclic ring structure is aromatic. Some examples of heteroaryl are pyridyl, furyl, pyrrolyl, thienyl, thiazolyl, oxazolyl, imidazolyl, indolyl, tetrazolyl, benzofuryl, xanthenes and dihydroindole. It is understood that any of the substitutable hydrogens on a heteroaryl can be substituted with halogen, $C_1$-$C_3$ alkyl, hydroxyl, alkoxy and cyano groups.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, a-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), tetracosahexaenoic acid (nisinic acid or all-cis-6,9,12,15,18,21-tetracosenoic acid) or lipoic acid.

The term "guanidine derivative" as used herein means the molecule known as metformin, phenformin, buformin, imeglimin or creatine and any derivative thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a fatty acid guanidine derivative or salicylate guanidine derivative and a pharmaceutically acceptable carrier. The invention includes a fatty acid guanidine derivative or salicylate guanidine derivative provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a fatty acid guanidine derivative or salicylate guanidine derivative is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a fatty acid guanidine derivative or salicylate guanidine derivative.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Compounds

Accordingly in one aspect, the present invention provides a molecular conjugate which comprises a guanidine derivative and a salicylic acid or fatty acid covalently linked, wherein the fatty acid is selected from the group consisting of omega-3 fatty acids and fatty acids that are metabolized in vivo to omega-3 fatty acids, wherein the conjugate comprises is capable of hydrolysis to produce free guanidine derivative and salicylic acid or free fatty acid.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, and tetracosahexaenoic acid. In other embodiments, the fatty acid is selected from eicosapentaenoic acid and docosahexaenoic acid. In some embodiments, the fatty acid is selected from lipoic acid. In some embodiments, the hydrolysis is enzymatic.

In another aspect, the present invention provides fatty acid guanidine derivatives or salicylic acid guanidine derivatives according to Formula I, Ia, Ib, Ic and Id:

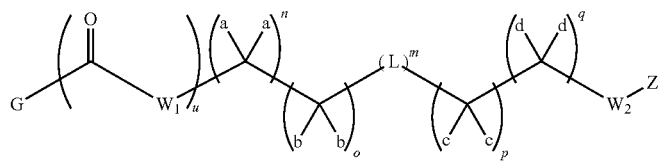

Formula I

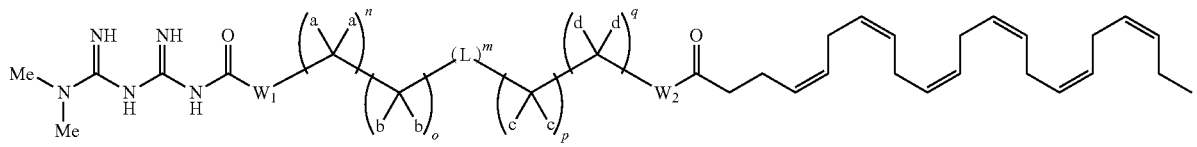

Formula Ia

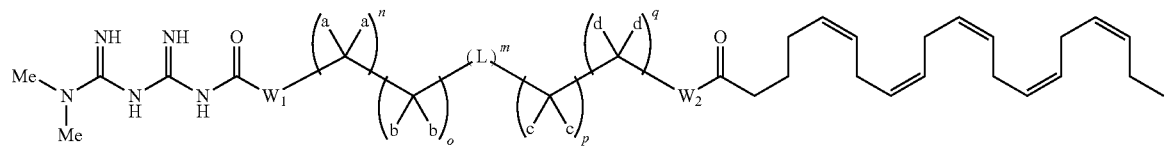

Formula Ib

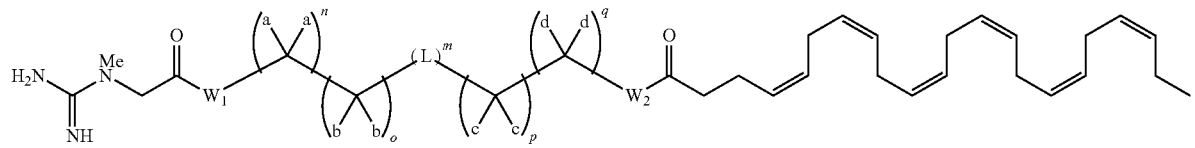

Formula Ic

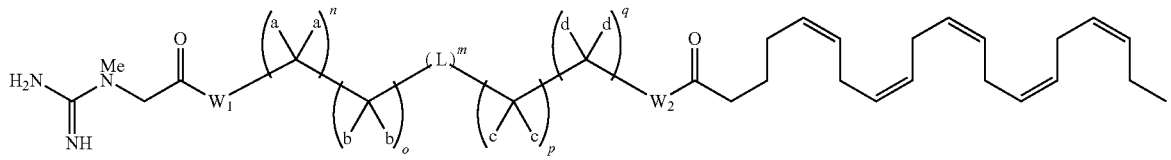

Formula Id and pharmaceutically acceptable salts, hydrates, solvates, prodrugs, enantiomers and stereoisomers thereof;
wherein
G, $R_1$, $R_2$, $R_3$, $W_1$, $W_2$, L, a, c, b, d, e, g, h, m, n, o, p, q, Z, r, s, t, u, v, z, $R_4$, $R_5$, $R_6$, $R_7$ and R are as defined above for Formula I, Ia, Ib, Ic and Id.

In some embodiments, one Z is

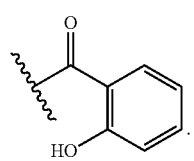

and r is 2.

In some embodiments, one Z is

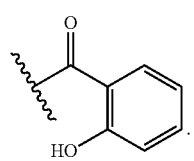

In some embodiments, one Z is

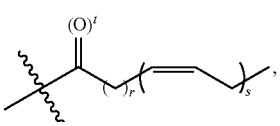

and r is 3.

In some embodiments, one Z is

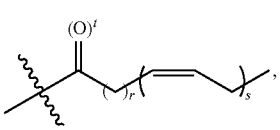

and r is 7.

In other embodiments, one Z is

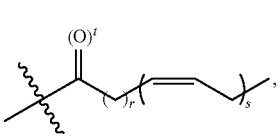

and s is 3.

In some embodiments, one Z is

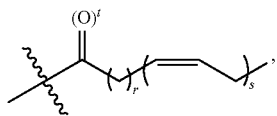

and s is 5.

In some embodiments, one Z is

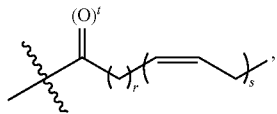

and s is 6.

In some embodiments, one Z is

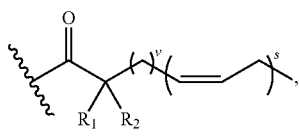

and v is 1.

In other embodiments, one Z is

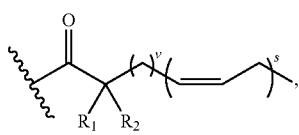

and v is 2.

In some embodiments, one Z is

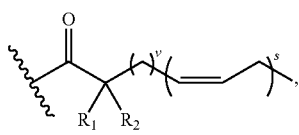

and v is 6.

In some embodiments, one Z is

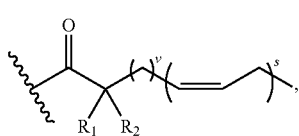

and s is 3.

In some embodiments, one Z is

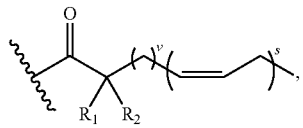

and s is 5.

In other embodiments, one Z is

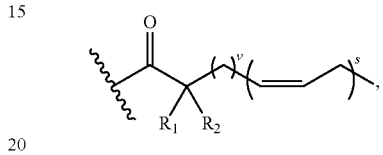

and s is 6.

In other embodiments, Z is

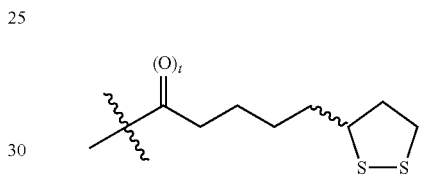

and t is 1.

In some embodiments, Z is

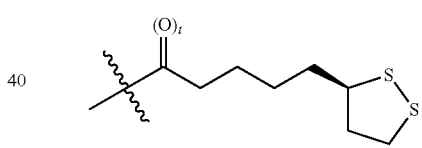

and t is 1.

In some embodiments, G is

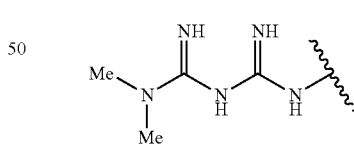

In some embodiments, G is

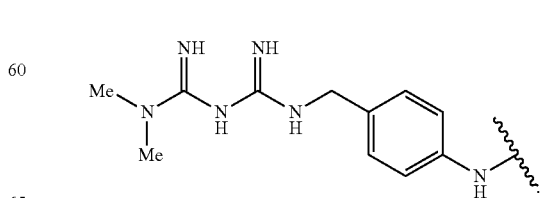

In some embodiments, G is

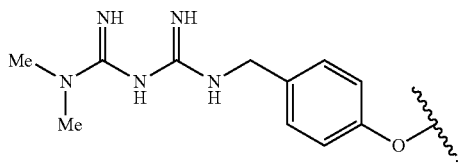

In some embodiments, G is

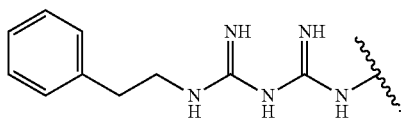

In some embodiments, G is

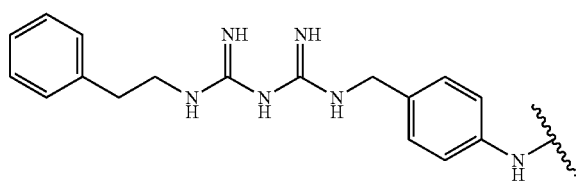

In some embodiments, G is

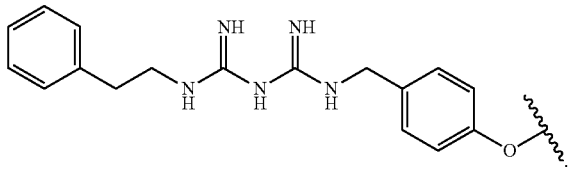

In some embodiments, G is

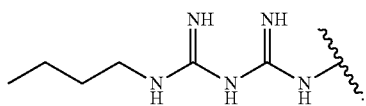

In some embodiments, G is

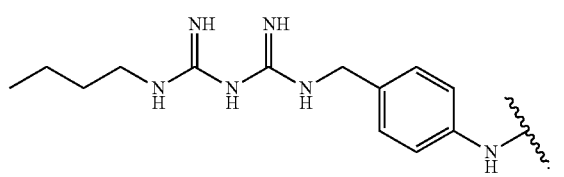

In some embodiments, G is

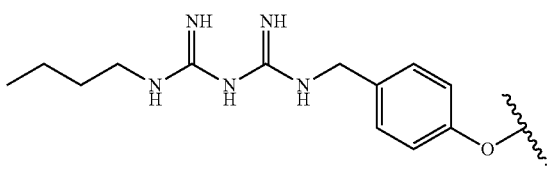

In some embodiments, G is

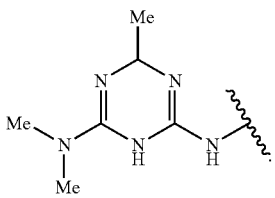

In some embodiments, G is

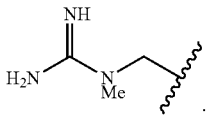

In some embodiments, G

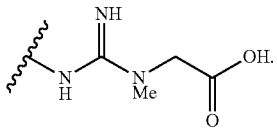 [SMILES: *NC(=N)N(C)CC(=O)O]

In some embodiments, $W_1$ is NH.
In some embodiments, $W_2$ is NH.
In some embodiments, $W_1$ is O.
In some embodiments, $W_2$ is O.
In some embodiments, $W_1$ is null.
In some embodiments, $W_2$ is null.
In some embodiments, $W_1$ and $W_2$ are each NH.
In some embodiments, $W_1$ and $W_2$ are each null.
In some embodiments, $W_1$ is O and $W_2$ is NH.
In some embodiments, $W_1$ and $W_2$ are each NR, and R is $CH_3$.
In some embodiments, m is 0.
In other embodiments, m is 1.
In other embodiments, m is 2.
In some embodiments, L is —S— or —S—S—.
In some embodiments, L is —O—.
In some embodiments, L is —C(O)—.
In some embodiments, L is heteroaryl.
In some embodiments, L is heterocycle.

In some embodiments, L is
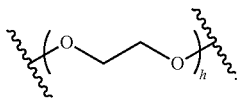
In some embodiments, L is
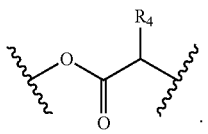
In some embodiments, L is
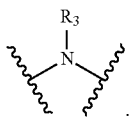
In some embodiments, L is
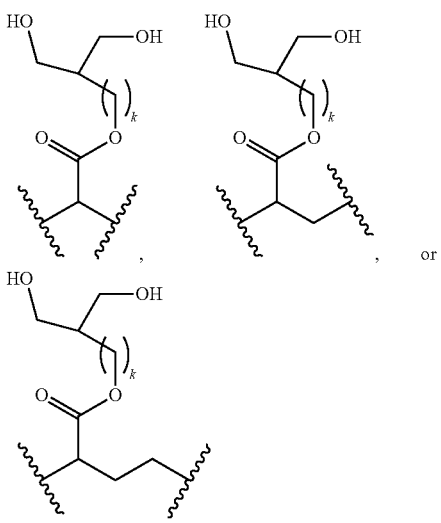
In some embodiments, L is
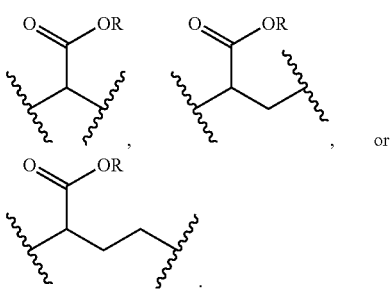
In some embodiments, L is
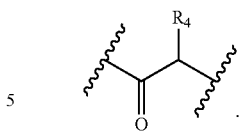
In some embodiments, L is
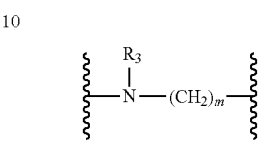
wherein m is 2.
In some embodiments, L is
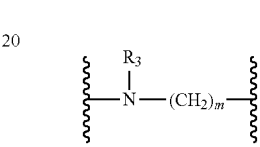
wherein m is 3.
In some embodiments, L is
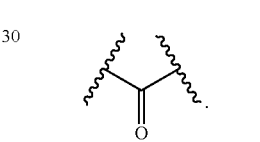
In some embodiments, L is
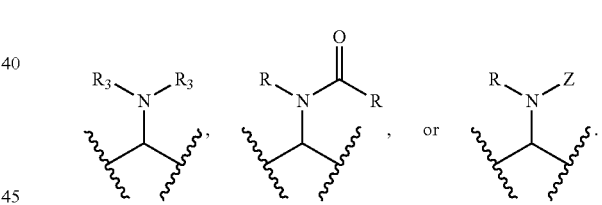
In some embodiments, L is
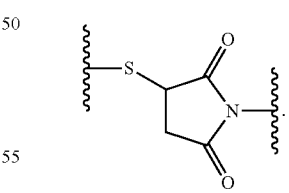
In some embodiments, L is
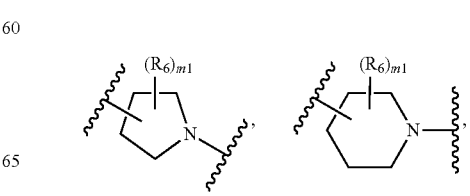

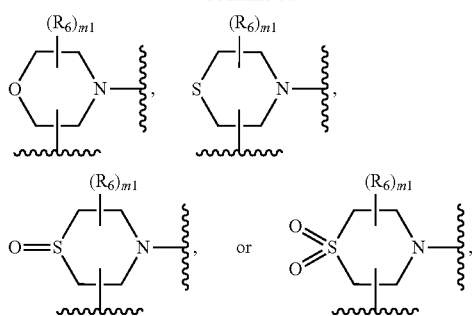

In some embodiments, L is

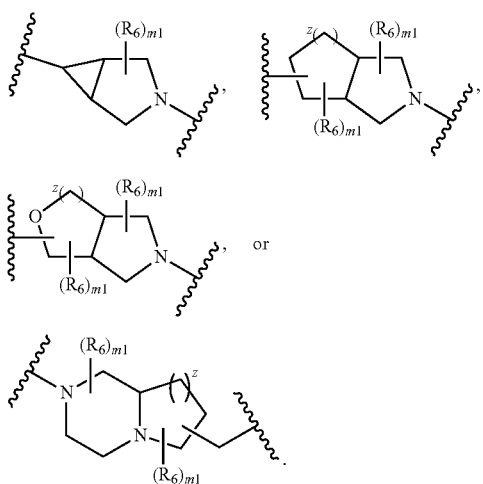

In some embodiments, L is

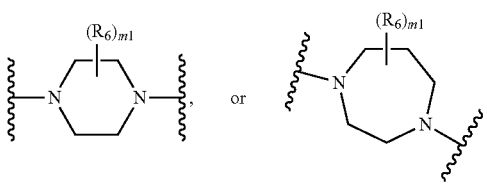

In some embodiments, L is

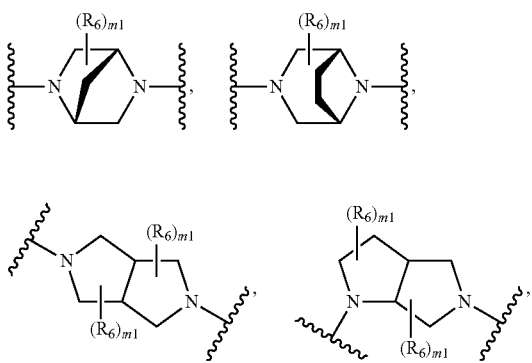

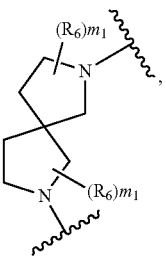 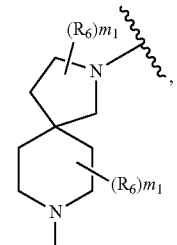 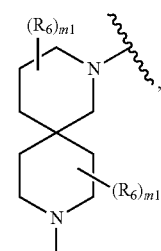

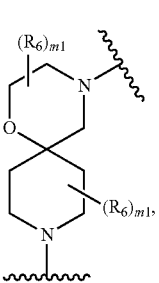 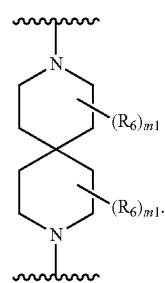

In other embodiments, one of n, o, p, and q is 1.
In some embodiments, two of n, o, p, and q are each 1.
In other embodiments, three of n, o, p, and q are each 1.
In some embodiments n, o, p, and q are each 1.
In some embodiments, one d is C(O)OR.
In some embodiments, r is 2 and s is 6.
In some embodiments, r is 3 and s is 5.
In some embodiments, t is 1.
In some embodiments, $W_1$ and $W_2$ are each NH, m is 0, n, and o are each 1, and p and q are each 0.
In some embodiments, $W_1$ and $W_2$ are each NH, m is 1, n, o, p, and q are each 1, and L is O.
In some embodiments, $W_1$ and $W_2$ are each NH, m is 1, n, o, p, and q are each 1, and L is

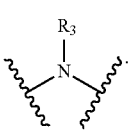

In some embodiments, $W_1$ and $W_2$ are each NH, m is 1, n, o, p, and q are each 1, and L is —S—S—.
In some embodiments, $W_1$ and $W_2$ are each NH, m is 1, n and o are each 0, p and q are each 1, and L is

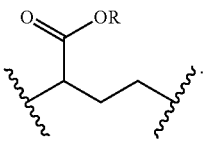

In some embodiments, $W_1$ and $W_2$ are each NH, m is 1, k is O, n and o are each 0, p and q are each 1, and L is

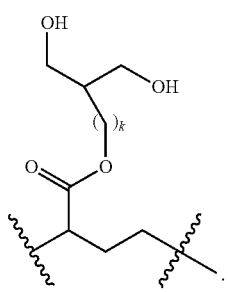

In some embodiments, $W_1$ and $W_2$ are each NH, m is 1, n and o are each 1, p and q are each 0, and L is

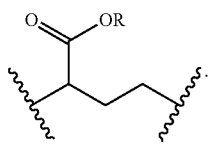

In some embodiments, $W_1$ and $W_2$ are each NH, m is 1, k is 0, n is 1, o, p and q are each 0, and L is

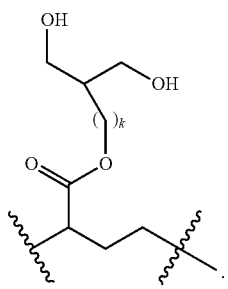

In some embodiments, $W_1$ and $W_2$ are each NH, m is 1, n, o, and p are each 0, and q is 1, and L is

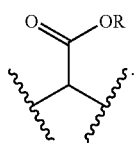

In some embodiments, $W_1$ and $W_2$ are each NH, m is 1, k is 1, n, o, and p are each 0, and q is 1, and L is

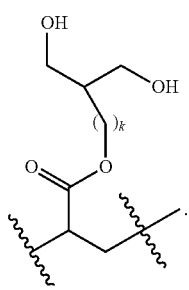

In some embodiments, $W_1$ and $W_2$ are each NH, m is 1, n is 1, and o, p, and q are each 0, and L is

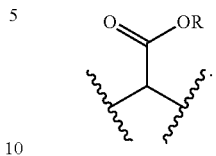

In some embodiments, $W_1$ and $W_2$ are each NH, m is 1, k is 1, o, p, and q are each 0, and L is

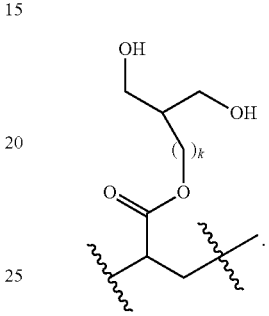

In some embodiments, $W_1$ and $W_2$ are each NH, m is 1, n, o, p, and q are each 1, and L is

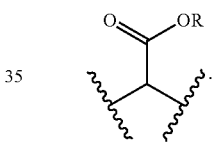

In some embodiments, $W_1$ and $W_2$ are each NH, m is 1, n, o, p, and q are each 1, and L is

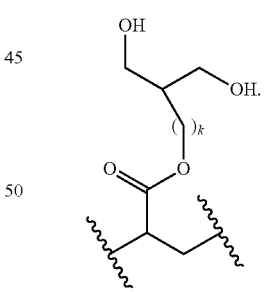

In some embodiments, $W_1$ and $W_2$ are each NH, m is 0, k is 1, o and p are each 1, and q is 0.

In some embodiments, $W_1$ and $W_2$ are each NH, m is 0, n, o, p, and q are each 1.

In some embodiments, $W_1$ and $W_2$ are each NH, m is 0, n and o are each 1, p and q are each 0, and each a is $CH_3$.

In some embodiments, $W_1$ and $W_2$ are each NH, m is 0, n and o are each 1, p and q are each 0, and each b is $CH_3$.

In some embodiments, $W_1$ and $W_2$ are each NH, m is 1, n, o, p, and q are each 1, $R_3$ is H, and L is

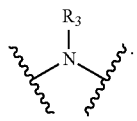

In some embodiments, $W_1$ and $W_2$ are each NH, m is 1, n, p and q are each 1, and o is 2, $R_3$ is H, and L is

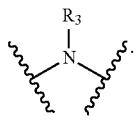

In some embodiments, $W_1$ and $W_2$ are each NH, m is 1, n, o, p are each 1, and q is 2, and L is

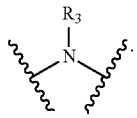

In some embodiments, $W_1$ and $W_2$ are each NH, m is 1, n, o, p, and q are each 1, and L is

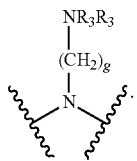

In some embodiments, $W_1$ and $W_2$ are each NH, m is 1, n and p are each 1, and o and q are each 0, and L is —C(O)—.

In some embodiments, $W_1$ and $W_2$ are each NH, m is 1, n and p are each 1, and o, and q are each 0, and L is

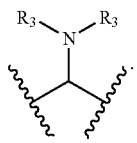

In some embodiments, $W_1$ and $W_2$ are each NH, m is 1, n, o, p, q are each 1, and L is

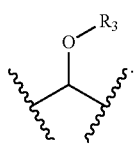

In some embodiments, $W_1$ and $W_2$ are each NH, m is 1, n, o, p, and q are each 1, h is 1, and L is

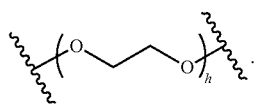

In some embodiments, $W_1$ and $W_2$ are each NH, m is 1, n, o, p, and q are each 1, and L is —S—.

In some embodiments, $W_1$ and $W_2$ are each NH, m is 1, n, o, p are each 0, q is 1, one d is —CH$_3$, and L is

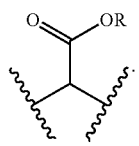

In some embodiments, $W_1$ and $W_2$ are each NH, m is 2, n, o, p, and q are each 0, one L is

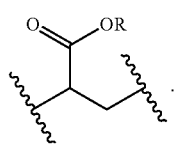

and one L is

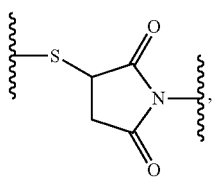 [SMILES: *SC1CC(=O)N(*)C1=O]

In some embodiments, m is 0, n, o, p, and q are each 0, and $W_1$ and $W_2$ are taken together to form an optionally substituted piperazine group.

In some embodiments, m is 1, n, o, p, and q are each 0, $W_1$ and $W_2$ are each null, and L is

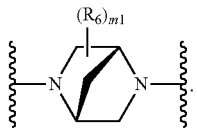

In some embodiments, m is 1, n and p are each 1, o and q are each 0, $W_1$ and $W_2$ are each NH, and L is $C_3$-$C_6$ cycloalkyl.

In some embodiments, m is 1, n is 1, o, p, and q are each 0, $W_1$ and $W_2$ are each NH, and L is $C_3$-$C_6$ cycloalkyl.

In some embodiments, m is 1, n, o, p, are each 0, q is 1, $W_1$ and $W_2$ are each NH, and L is $C_3$-$C_6$ cycloalkyl.

In some embodiments, m is 1, n, o, p, and q are each 0, $W_1$ is NH, $W_2$ is null, and L is

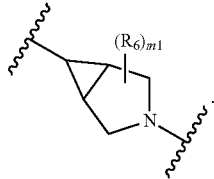

In some embodiments, m is 1, n o, p, and q are each 0, $W_1$ is null, $W_2$ is NH, and L is

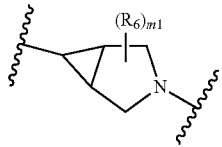

In some embodiments, m is 1, n o, p, and q are each 0, $W_1$ is NH, $W_2$ is null, and L is

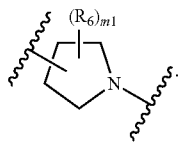

In some embodiments, m is 1, n o, p, and q are each 0, $W_1$ is null, $W_2$ is NH, and L is

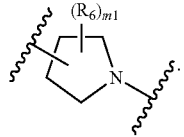

In some embodiments, m is 1, n is 1, o, p, and q are each 0, $W_1$ is NH, $W_2$ is null, and L is

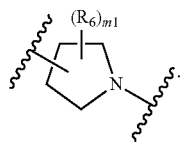

In some embodiments, m is 1, n, o, p, are each 0, q is 1, $W_1$ is null, $W_2$ is NH, and L is

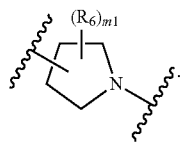

In some embodiments, m is 1, n, o, p, and q are each 0, $W_1$ is NH, $W_2$ is null, and L is

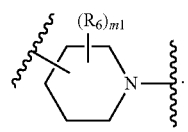

In some embodiments, m is 1, n, o, p, and q are each 0, $W_1$ is null, $W_2$ is NH, and L is

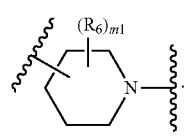

In some embodiments, m is 1, n is 1, o, p, and q are each 0, $W_1$ is NH, $W_2$ is null, and L is

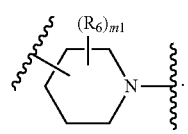

In some embodiments, m is 1, n, o, p, are each 0, q is 1, $W_1$ is null, $W_2$ is NH, and L is

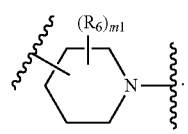

In some embodiments, m is 1, n is 1, o, p, and q are each 0, $W_1$ is NH, $W_2$ is null, and L is

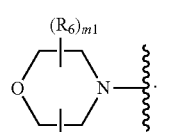

In some embodiments, m is 1, n, o, p, are each 0, q is 1, $W_1$ is null, $W_2$ is NH, and L is

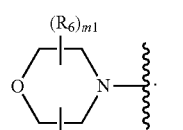

In some embodiments, m is 1, n, o, p, q are each 0, $W_1$ and $W_2$ is null, and L is

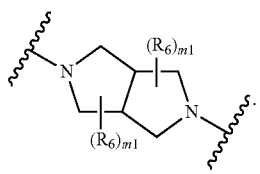

In some embodiments, m is 1, n, o, p, q are each 0, $W_1$ and $W_2$ is null, and L is

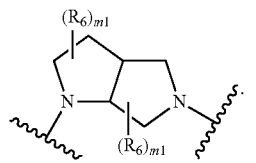

In some embodiments, m is 1, n, o, p, q are each 0, $W_1$ is NH, $W_2$ is null, and L is

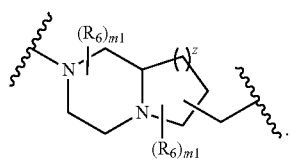

In some embodiments, m is 1, n, o, p, q are each 0, $W_1$ is null, $W_2$ is NH, and L is

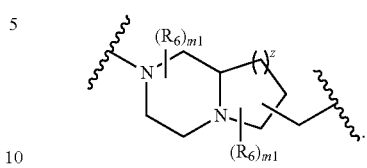

In some embodiments, m is 1, n, o, p, are each 0, q is 1, $W_1$ and $W_2$ are each and NH, is null, L is

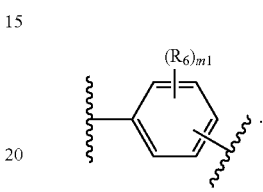

In some embodiments, m is 1, n, o, p, are each 0, q is 1, $W_1$ and $W_2$ are each NH, is null, and L is a heteroaryl.

In some of the foregoing embodiments, r is 2, s is 6 and t is 1.

In some of the foregoing embodiments, r is 3, s is 5 and t is 1.

In Formula I, Ia, Ib, Ic and Id any one or more of H may be substituted with a deuterium. It is also understood in Formula I, Ia, Ib, Ic and Id that a methyl substituent can be substituted with a $C_1$-$C_6$ alkyl.

In other illustrative embodiments, compounds of Formula I are as set forth below:

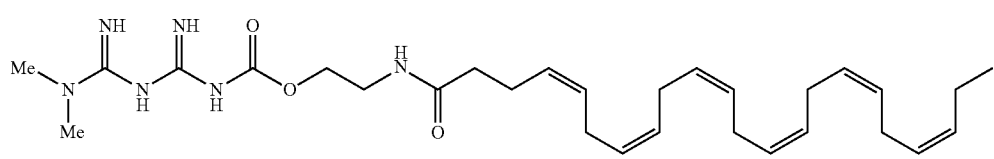

I-1

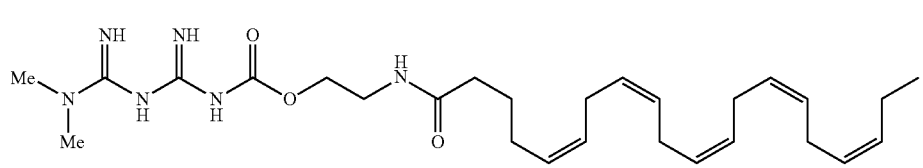

I-2

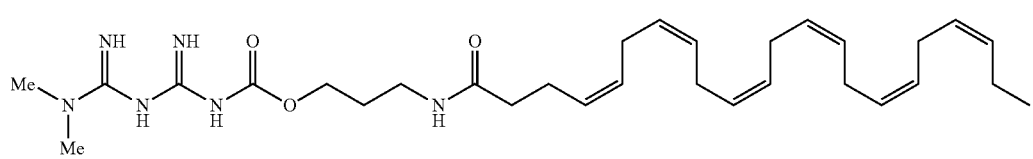

I-3

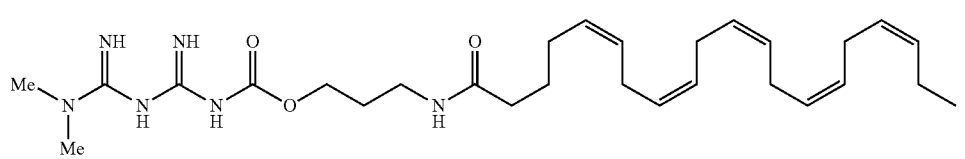

I-4

-continued
I-5
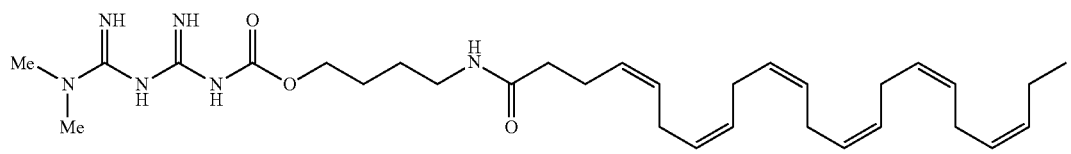
I-6
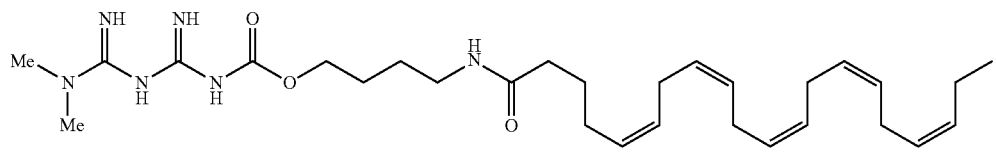
I-7
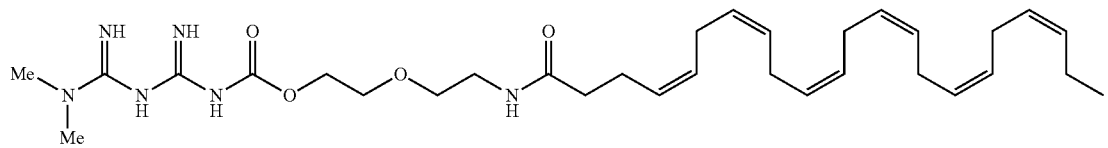
I-8
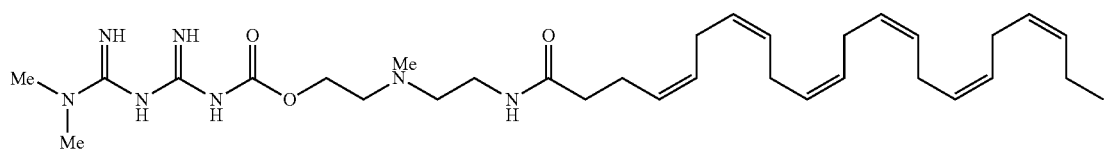
I-9
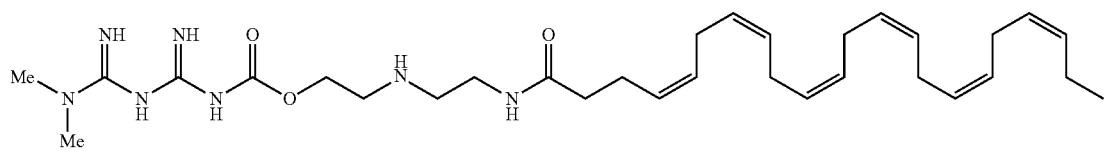
I-10
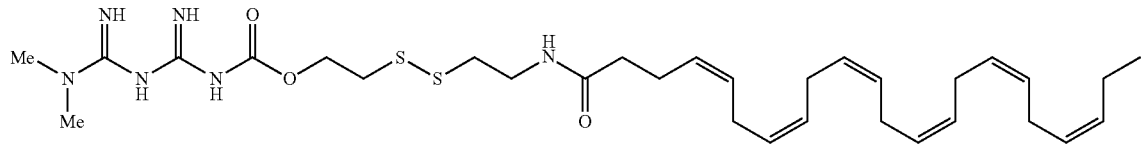
I-11
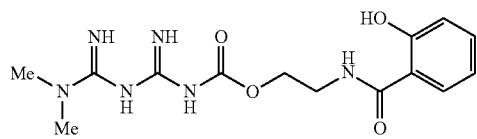
I-12
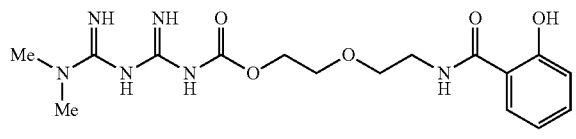
I-13
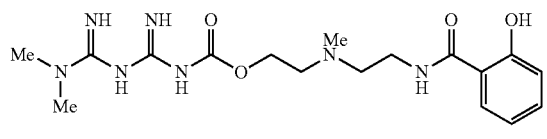
I-14
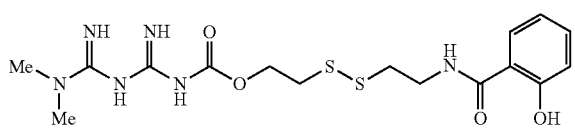
I-15
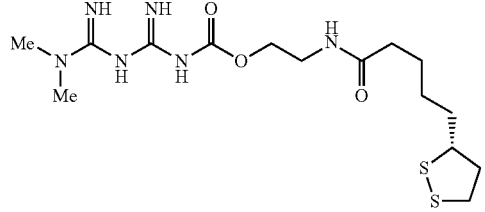
I-16
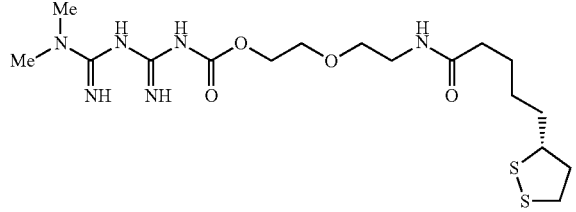

-continued
I-17
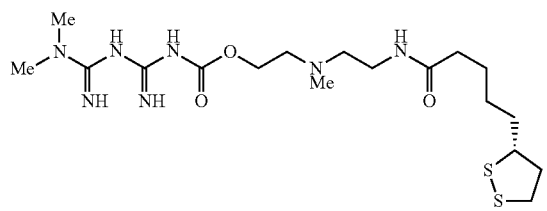
I-18
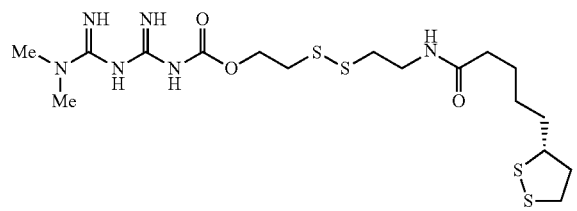
I-19
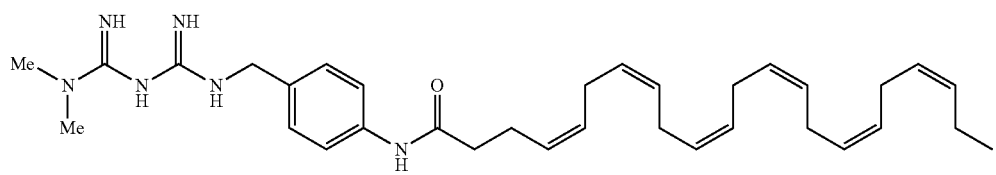
I-20
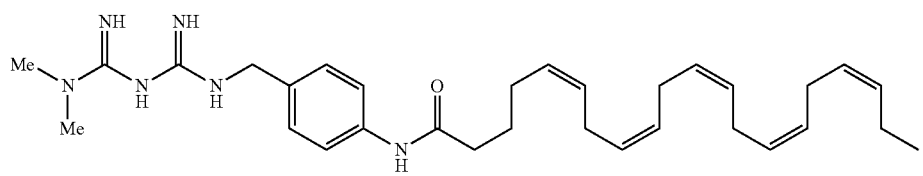
I-21
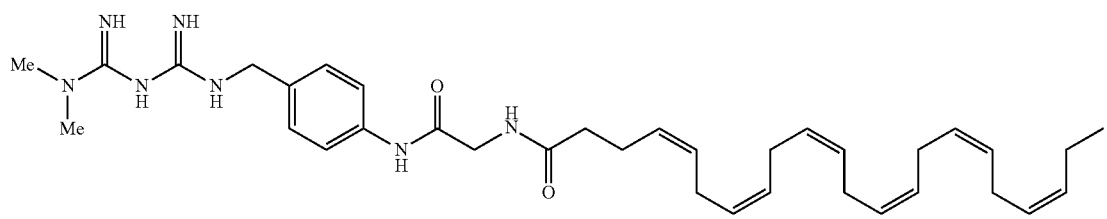
I-22
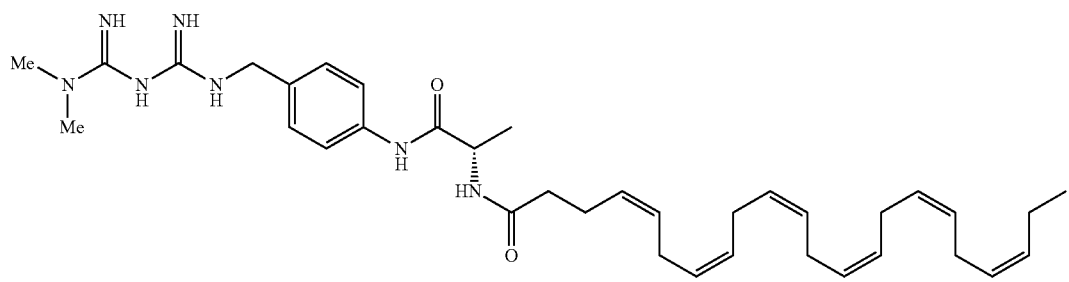
I-23
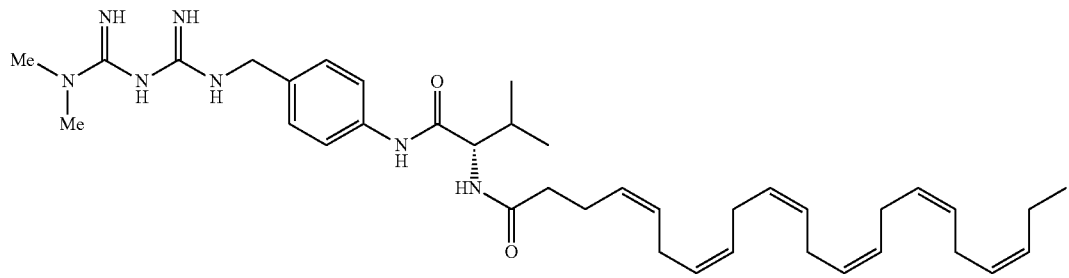
I-24
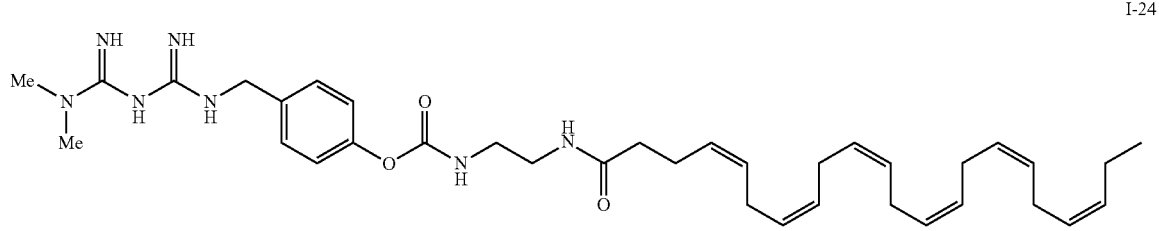

I-25
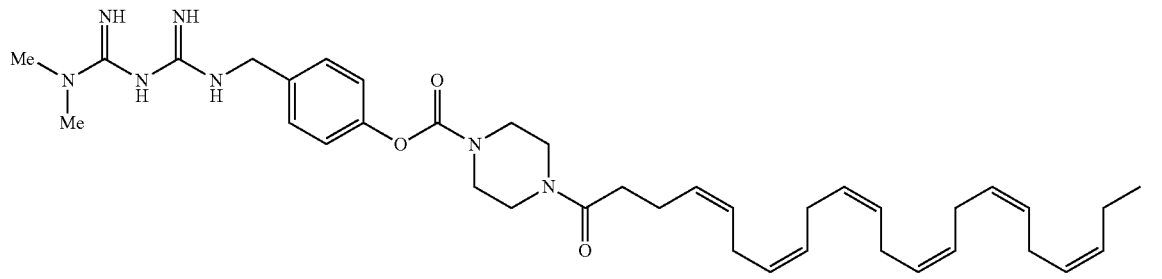
I-26
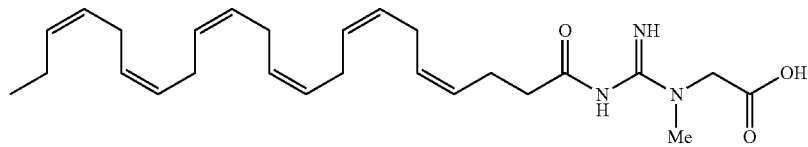
I-27
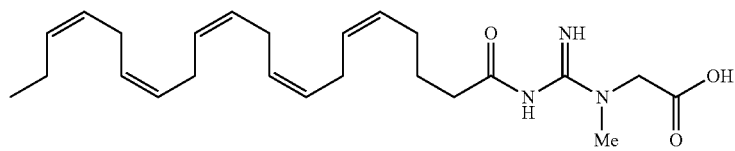
I-28
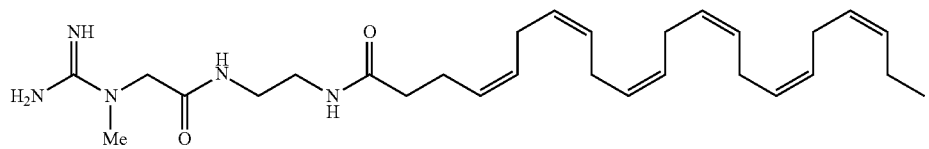
I-29
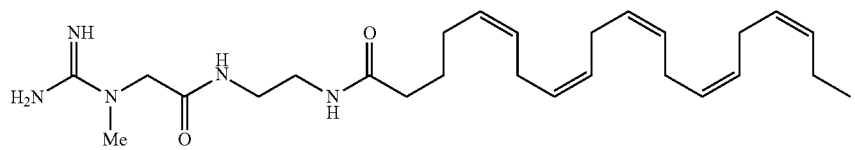
I-30
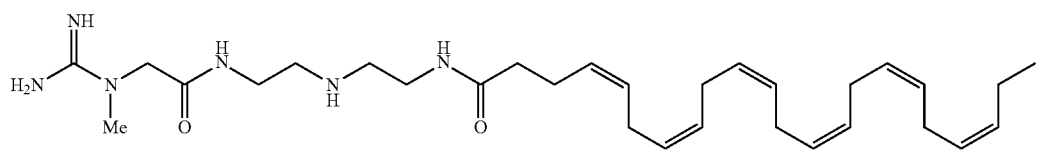
I-31
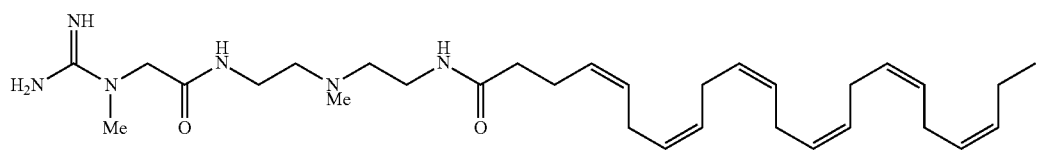
I-32
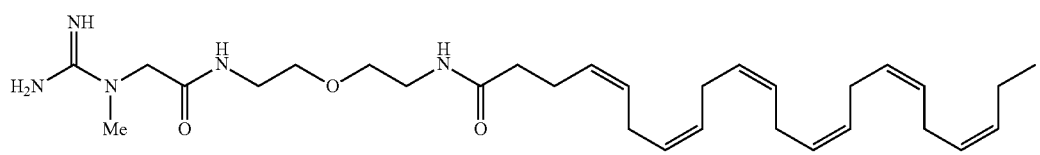
I-33
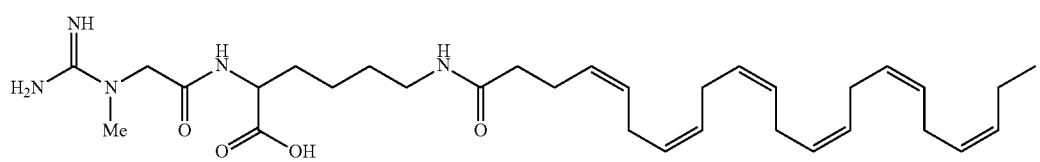

-continued
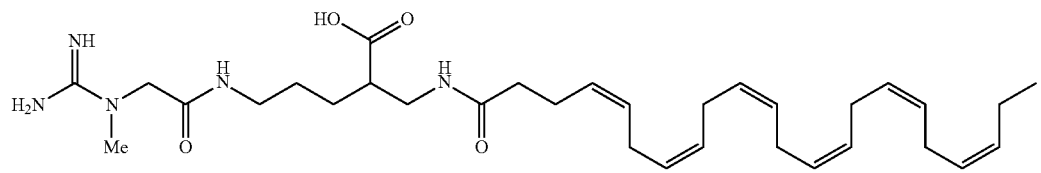
I-34
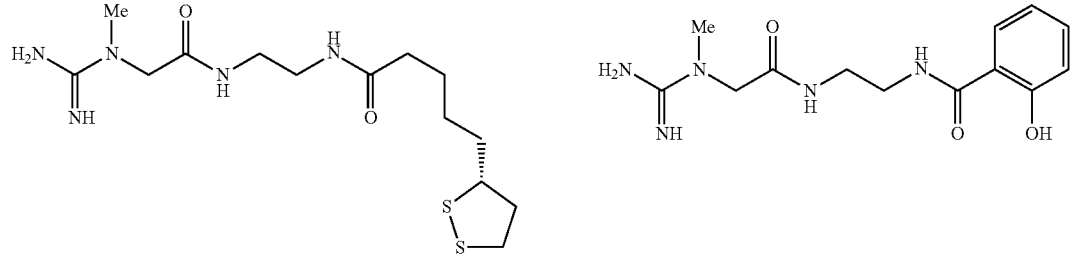
I-35
I-36
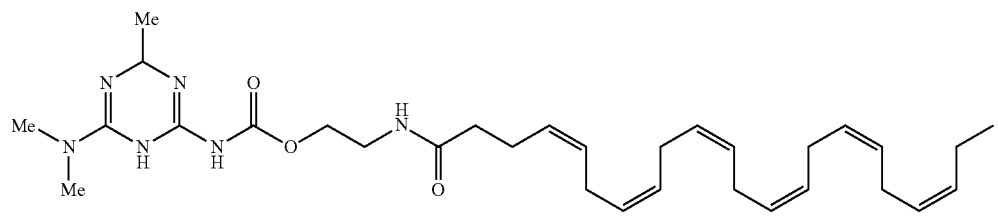
I-37
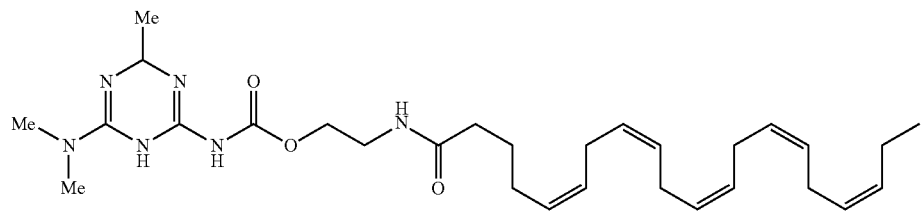
I-38
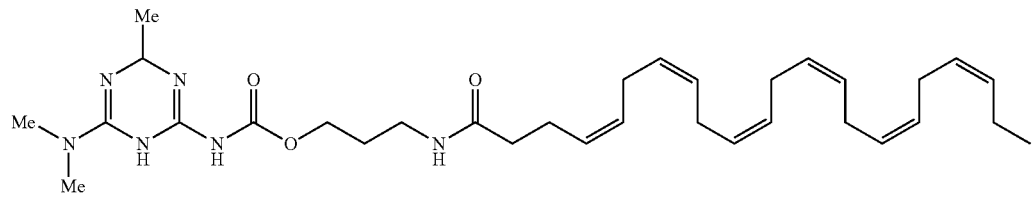
I-39
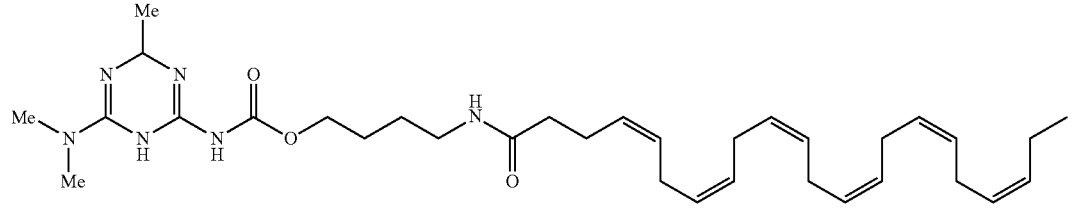
I-40
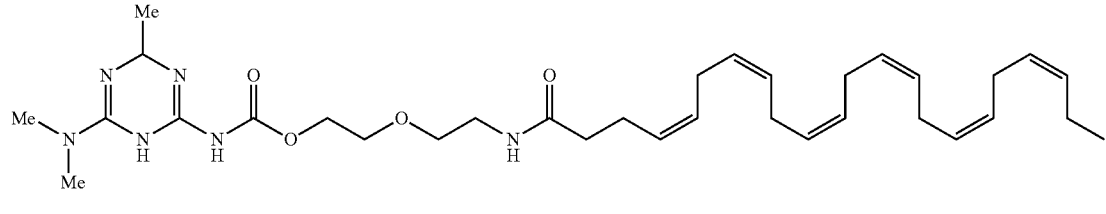
I-41
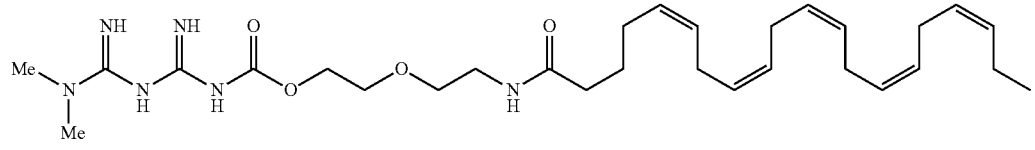
I-42

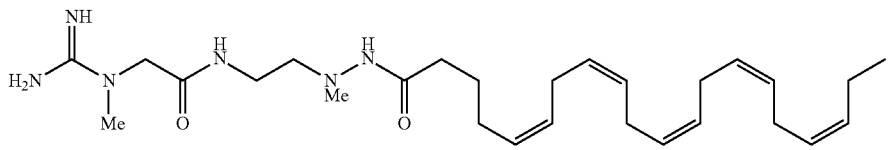

I-43

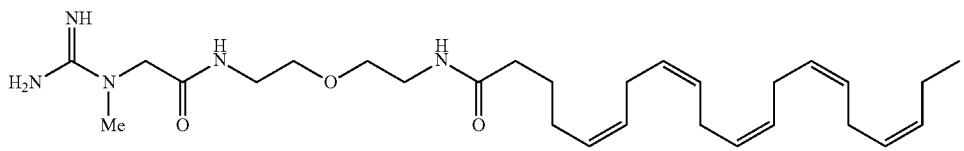

I-44

Methods for Using Fatty Acid Guanidine or Salicylate Guanidine Derivatives

The invention includes methods for the treatment or prevention of metabolic diseases including diabetic nephropathy, chronic kidney disease (CKD), atherosclerosis, dyslipidemia, coronary heart disease, hypercholesterolemia, Type 2 diabetes, elevated cholesterol, metabolic syndrome, polycystic ovary syndrome and cardiovascular disease. In addition, they are useful in the treatment of autoimmune diseases such as rheumatoid arthritis, cystic fibrosis, inflammatory bowel diseases (including colitis and Crohn's disease)

In one embodiment, the method comprises contacting a cell with a fatty acid guanidine derivative or salicylate guanidine derivative in an amount sufficient to improve renal function in type 1 or type 2 patients with diabetic nephropathy or patients with chronic kidney disease (CKD).

Also provided in the invention is a method for inhibiting, preventing, or treating a metabolic disease, or symptoms of a metabolic disease, in a subject. Examples of such disorders include, but are not limited to atherosclerosis, dyslipidemia, hypertriglyceridemia, hypertension, heart failure, cardiac arrhythmias, low HDL levels, high LDL levels, sudden death, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, carotid atherosclerosis, peripheral arterial disease, diabetic nephropathy, hypercholesterolemia in HIV infection, acute coronary syndrome (ACS), non-alcoholic fatty liver disease, arterial occlusive diseases, cerebral arteriosclerosis, cerebrovascular disorders, myocardial ischemia, polycystic ovary syndrome and diabetic autonomic neuropathy.

In some embodiments, the subject is administered an effective amount of a fatty acid guanidine derivative or salicylate guanidine derivative.

The invention also includes pharmaceutical compositions useful for treating or preventing a metabolic disease, or for inhibiting a metabolic disease, or more than one of these activities. The compositions can be suitable for internal use and comprise an effective amount of a fatty acid guanidine derivative or salicylate guanidine derivative and a pharmaceutically acceptable carrier. The fatty acid guanidine derivative or salicylate guanidine derivatives are especially useful in that they demonstrate very low peripheral toxicity or no peripheral toxicity.

The fatty acid guanidine derivative or salicylate guanidine derivative can each be administered in amounts that are sufficient to treat or prevent a metabolic disease or prevent the development thereof in subjects.

Administration of the fatty acid guanidine derivative or salicylate guanidine derivative derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid guanidine derivative or salicylate guanidine derivative derivative and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the fatty acid guanidine derivative or salicylate guanidine derivative derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid metformin derivatives.

The fatty acid guanidine derivative or salicylate guanidine derivative derivatives can be also formulated as a suppository that can be prepared from fatty emulsions or suspensions; using polyalkylene glycols such as propylene glycol, as the carrier.

The fatty acid guanidine derivative or salicylate guanidine derivative derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

The fatty acid guanidine derivative or salicylate guanidine derivative an also be delivered by the use of monoclonal antibodies as individual carriers to which the fatty acid guanidine derivatives or salicylate guanidine derivatives are coupled. The fatty acid guanidine derivative or salicylate guanidine derivative can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the fatty acid guanidine derivatives or salicylate guanidine derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, fatty acid guanidine derivative or salicylate guanidine derivative is not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 90%, from about 10% to about 90%, or from about 30% to about 90% of the fatty acid guanidine derivative or salicylate guanidine derivative by weight or volume.

The dosage regimen utilizing the fatty acid guanidine derivative or salicylate guanidine derivative is selected in accordance with a variety of factors including type, species, age, weight, sex and medical condition of the patient; the severity of the condition to be treated; the route of administration; the renal or hepatic function of the patient; and the particular fatty acid guanidine derivative or salicylate guanidine derivative employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid guanidine derivative or salicylate guanidine derivative per day. Compositions for in vivo or in vitro use can contain about 20, 50, 75, 100, 150, 250, 500, 750, 1,000, 1,250, 2,500, 3,500, or 5,000 mg of the fatty acid metformin derivative. In one embodiment, the compositions are in the form of a tablet that can be scored. Effective plasma levels of the fatty acid guanidine derivative or salicylate guanidine derivative derivative can range from about 5 ng/mL to 5000 ng/mL. Appropriate dosages of the fatty acid guanidine derivatives or salicylate guanidine derivatives can be determined as set forth in Goodman, L. S.; Gilman, A. *The Pharmacological Basis of Therapeutics,* 5th ed.; MacMillan: New York, 1975, pp. 201-226.

Fatty acid guanidine derivatives or salicylate guanidine derivatives can be administered in a single daily dose, or the total daily dosage can be administered in divided doses of two, three or four times daily. Furthermore, fatty acid guanidine derivatives or salicylate guanidine derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the fatty acid guanidine derivative or salicylate guanidine derivative ranges from about 0.1% to about 15%, w/w or w/v.

Methods of Making

Methods for Making the Fatty Acid Guanidine Derivatives or Salicylate Guanidine Derivatives Examples of synthetic pathways useful for making fatty acid guanidine derivatives or salicylate guanidine derivatives of Formula I, Ia, Ib, Ic and Id are set forth in the Examples below and generalized in Schemes 1-4.

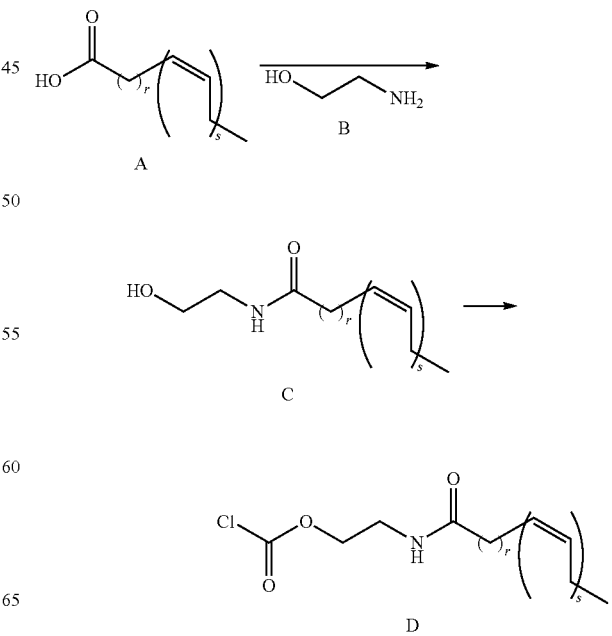

Scheme 1

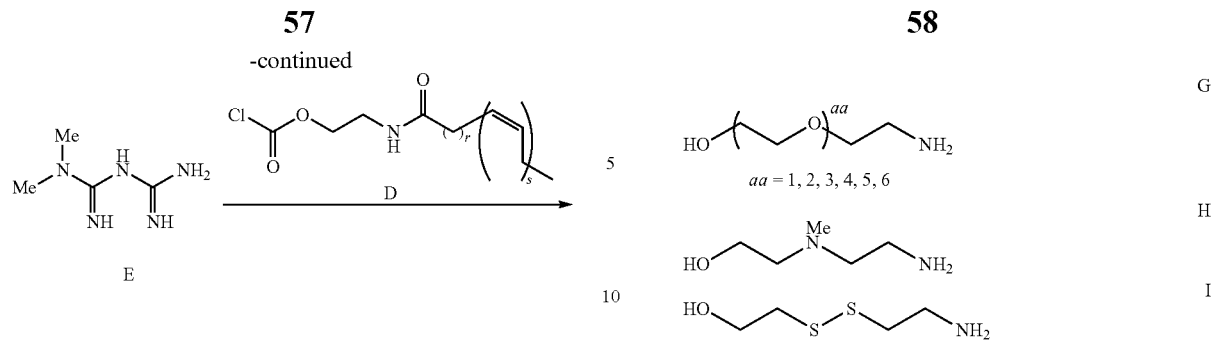

wherein $R_3$, $R_7$, $R_8$, r and s are as defined above.

A fatty acid of the general formula A can be coupled with ethanolamine B in the presence of EDC or HATU in a solvent such as acetonitrile or dichloromethane to form compound of the general formula C. Compound C can be reacted with either triphosgene or phosgene to form compound D. Compound D can then be reacted with metformin E to afford compounds of the general formula F, according to the procedures outlined in Huttunen et al, *Synthesis* 2008, p. 3619-3624. To those familiar in the art, the fatty acid of the general formula A can also be substituted with either lipoic acid or salicylic acid. Furthermore, compound E can also be substituted with phenformin or buformin or a guanidine derivative of the formula E1:

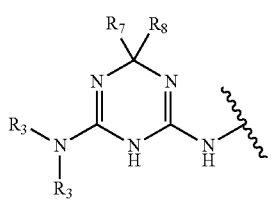

E1

Also, to those familiar in the art, ethanolamine B can also be substituted with other amino alcohols such as 3-aminopropanol, 4-aminobutanol or the ones shown in G, H, and I. The pegylated amino alcohols of the general formula G (wherein aa=1, 2, 3, 4, 5, 6) and the diamino alcohol H are commercially available. The amino alcohol of the formula I can be prepared according to the procedures outlined in Van Rensburg et al, *Archives of Biochemistry and Biophysics* 1967, 118, p. 531-5.

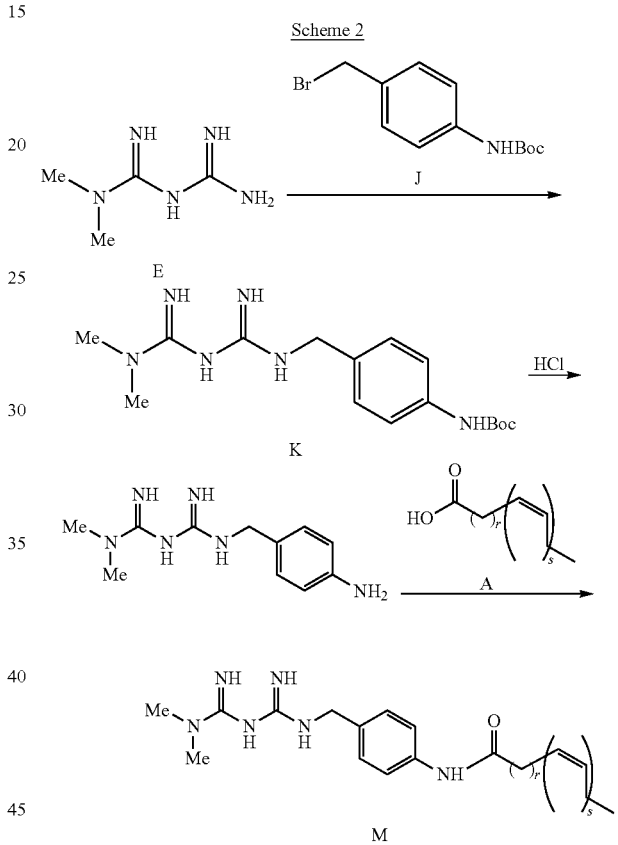

wherein r and s are as defined above.

Metformin E can be reacted with the commercially available reagent J to form compound of the general formula K. The Boc group is removed by treatment with an acid such as HCl or TFA to afford derivative L. Compound L can be reacted with fatty acid A to afford compounds of the general formula M.

Scheme 3

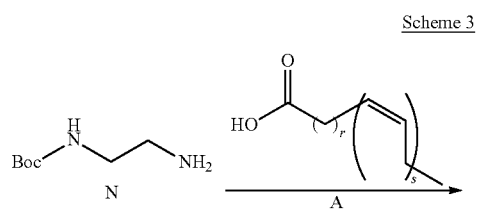

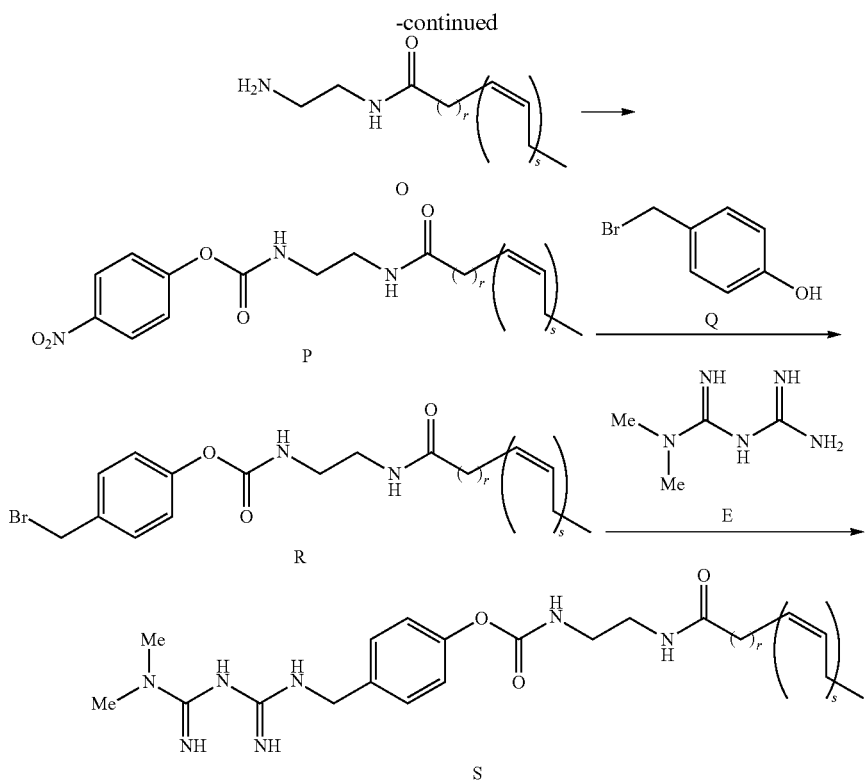

wherein r and s are as defined above.

The commercially available mono-Boc protected ethylenediamine N can be coupled with fatty acid A in the presence of EDC or HATU in either acetonitrile or dichloromethane. The resulting amide can be treated with an acid such as HCl or THA to obtain the amine derivative O. Compound O can be reacted with 4-nitrophenyl chloroformate to obtain derivative P. Compound P can be reacted with the commercially available phenol derivative Q to obtain compounds of the general formula R. Compound R can then be reacted with metformin E to obtain compounds of the general formula S. To those familiar in the art, the mono-Boc protected ethylenediamine N can also be substituted with a variety of mono-protected diamines A variety of BOC-protected diamines are commercially available. The following diamines can be prepared according to the procedures outlined in the corresponding references:

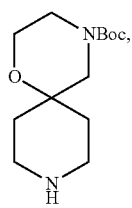

DA1

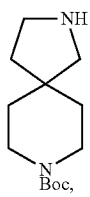

DA2

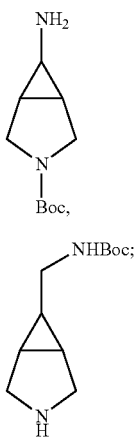

DA3

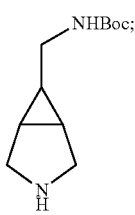

DA4

(Diamine DA1, Stocks et al, Bioorganic and Medicinal Chemistry Letters 2010, p. 7458; diamine DA2, Fritch et al, Bioorganic and Medicinal Chemistry Letters 2010, p. 6375; diamine DA3 and DA4, Moffat et al, J. Med. Chem. 2010, 53, p. 8663-8678). To those familiar in the art, detailed procedures to prepare a variety of mono-protected diamines can also be found in the following references: WO 2004092172, WO 2004092171, and WO 2004092173.

Scheme 4

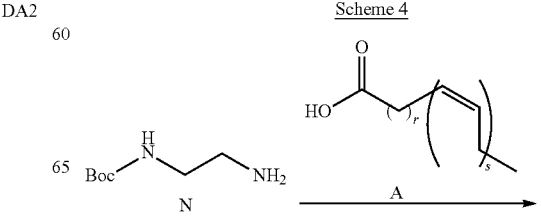

-continued

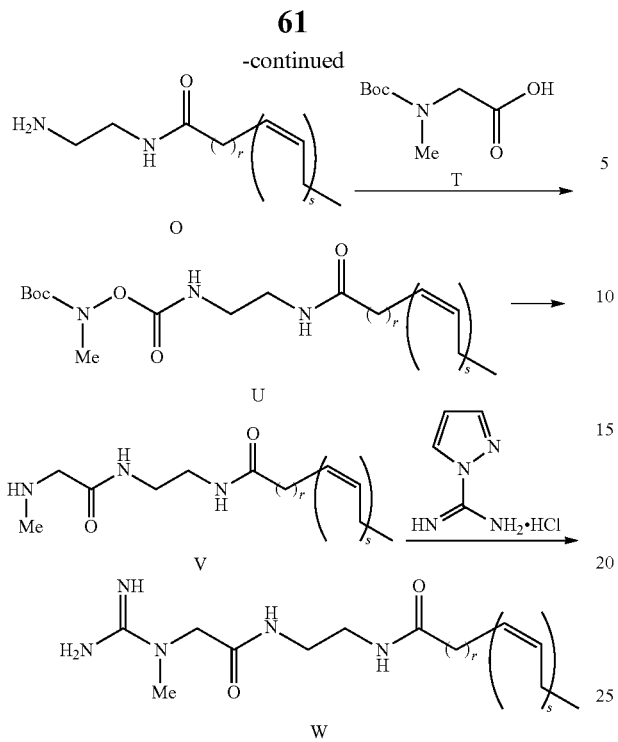

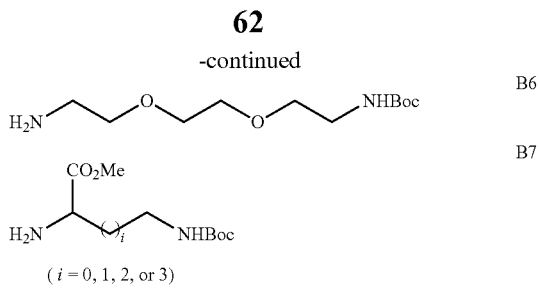

wherein r and s are as defined above.

The mono-Boc protected ethylenediamine N can be coupled with a fatty acid of the formula A using EDC or HATU in a solvent such as acetonitrile or dichloromethane to afford O. Compound O can be coupled with an amino acid of the formula T to afford U. This compound can then be treated with an acid such as TFA or HCl to afford the amine derivative V. Compound V can be treated with the HCl salt of 1H-pyrazole-1-carboximidamide (commercially available) to afford compound W. To those familiar in the art, the mono-Boc amine N can be substituted with a variety of other mono-Boc diamine described earlier in Scheme 3. In addition, the following type of functionalized mono-Boc protected diamine (B1-B7) can also be used. Detailed procedures, along with the references that are needed to prepare the corresponding amines B1-B7 are described in the following patent application: Vu et al "Preparation of fatty acid acylated salicylates for the treatment of inflammatory disorders" US 20100184730.

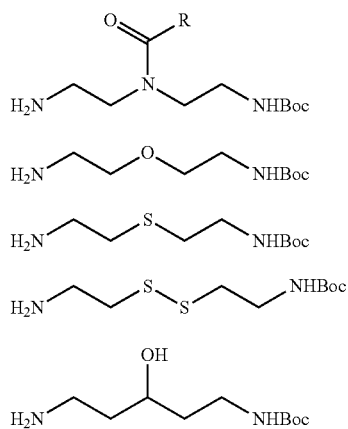

($i$ = 0, 1, 2, or 3)

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NF-κB signaling axis. The compounds of this invention inhibit the transcriptional activation of NF-κB and thus decrease the production and release of TNFα. Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 mm² tissue culture flask (cells should be at ~70% confluence) and add 10 ml of warmed complete growth media (DMEM+10% FBS+1×pen/step). The cells are scraped into suspension using a sterile plate scraper and homogenized by pipetting up and down with a 10 ml serological pipette. The cell concentration is determined using a clinical hematoctyometer. Cells are then diluted to 150,000 cells per ml into growth media. The diluted cells are then transferred to a sterile reagent reservoir and 100 μl of cell suspension is pipetted into each well of a 96 well culture plate using a multichannel pipette (15,000 cells/well). Plates are then incubated at 37° C. under normal tissue culture growth conditions (37° C., humidified CO₂ chamber).

Day 2: The test compound sample plate is prepared. Test compounds are prepared in growth media. Compounds are delivered to media from 1000× stocks in 100% DMSO (e.g. for a 10 μM final concentration of test compound, deliver 2 μl of 10 mM test compound to 2 ml of media). At least 150 μl of 1× compound in media is added to 96 well sample plate. Note: the perimeter wells of the 96 well plate are not used to avoid edge effects. Twelve sample wells are prepared with media plus 0.1% DMSO (these samples will serve as the vehicle controls; LPS-stimulated and non-stimulated. 10 μM dexamethasone is used as a positive control). Culture plates are then returned to the growth incubator for 2 hours. Cells are stimulated afterwards by adding 25 μl of 50 ng/ml LPS is added to every well (except the 6 unstimulated vehicle control wells: final concentration of 10 ng/ml LPS. Plates are returned to growth incubator for 3 hours. Afterwards, 100 μl of media supernatant is removed and transferred to a 96 well v-bottom sample plate. The media supernatant plate is centrifuged for 5 minutes at 1000 rpm in a swing-bucket centrifuge, pelleting any cellular debris that may remain in supernatant. 80 μl of supernatant is removed from sample plate and transferred to a fresh v-bottom 96 well plate. Cell viability is measured using Celltiter-glo kit. By measuring cell viability, a given compound's effects on TNFα secretion can show whether such effects are due to cytotoxicity or to inhibition of inflammatory signaling. 100 μl of Celltiter-glo reagent are added to each well of the cell culture plate and afterwards measure the luminescence signal (CPS) of the plate is measured using the Victor 5 plate reader (0.3 second read; 60 second plate shaking prior to read). Cell viability of a given compound at a given concentration is computed as follows:

Cell viability=CPS Sample/(Average CPS unstimulated controls)*100

Mouse TNFα ELISA

Place 20 μl of media supernatant in each well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, OD 450 nm is measured using the Victor 5 plate reader (0.1 second/well scan). The TNFα secretion percent of control is then determined by using the formula:

100×($OD$ 450 nm Sample $X$)−(Average $OD$ 450 nm unstimulated vehicle controls)/(Average $OD$ 450 nm $LPS$ stimulated vehicle controls)−(Average $OD$ 450 nm unstimulated vehicle controls)

For each test compound, TNFα secretion percent of control is plotted as a function of compound concentration using a four parameter dose-response curve fit equation (XLFIT Model #205):

fit=$(A+((B-A)/(1+((C/x)^D))))$ inv=$(C/((((B-A)/(y-A))-1)^(1/D)))$ res=$(y-\text{fit})$ Example 2

Effects of the Compounds of the Invention on NFκB Levels in RAW 264.7 Macrophages RAW 264.7 cells transfected with an NFκB-driven luciferase reporter are plated in 96 well plates. Cells are treated with Vehicle (0.1% ethanol) or test compounds for 2 hours. As a positive control for inhibition of NFκB signaling, 6 wells are treated with 10 μM dexamethasone. Cells are then challenged with 200 ng/mL LPS for 3 hours in the presence of test compounds. A subset of wells treated with vehicle should remain unstimulated with LPS to determine the floor signal of the assay. NFκB driven luciferase activity is developed by addition of BriteLite luciferase kit (Perkin-Elmer) and measured using a Victor V plate reader. NFκB activity (luciferase activity) for each treatment was normalized to Vehicle wells treated with LPS (% NFκB Response). AlamarBlue was used to monitor cell viability to ensure that inhibition of luciferase signal was not a result of compound cytotoxicity.

Example 3

In Vivo Effects of Compounds of the Invention in an LPS-Challenge TNFα Mouse Model To measure the effects of compounds on TNFα secretion in vivo, Male Swiss Webster mice (n=10 animals per group) are dosed by oral gavage with each test compound. All compounds are formulated in an aqueous solution of 0.5% carboxymethylcellulose and 0.05% TWEEN-80 (Vehicle). One hour after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2,000×g. Serum is harvested from tubes (100-150 μl per animal) and frozen at −70° C. TNFα serum levels are measured using commercially available TNFα ELISA kits (*p<0.05 using a 2-tailed t-test).

Example 4

In Vivo Effects of Compounds of the Invention in Zucker Fatty Rats and Ob/Ob Mice Twelve-week-old male Zucker fa/fa rats and 8-week-old ob/ob (Lepob/ob) and ob/1 mice are given free access to food and water. A compound of the invention (120 mg/kg/day) is dosed orally by gavage once per day. For glucose tolerance tests, glucose (2.0 g/kg) is administered by oral gavage (rats) or intraperitoneal injection (mice) after an overnight fast. Blood glucose and serum insulin concentrations are determined during oral glucose tolerance tests in Zucker fa/fa rats or fa/1 rats. For insulin tolerance tests, insulin (2.0 U/kg) is injected intraperitoneally after an overnight fast. Cholesterol, triglyceride, long-chain FFA, and ALT concentrations are measured in sera from fasting Zucker fa/fa rats.

Compounds

The following non-limiting compound examples serve to illustrate further embodiments of the fatty acid guanidine derivatives. It is to be understood that any embodiments listed in the Examples section are embodiments of the fatty acid guanidine derivatives and, as such, are suitable for use in the methods and compositions described above.

Example 5

Preparation of Compound I-3

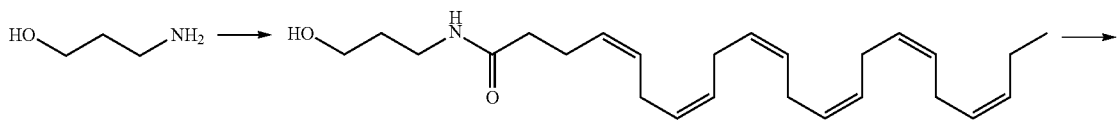

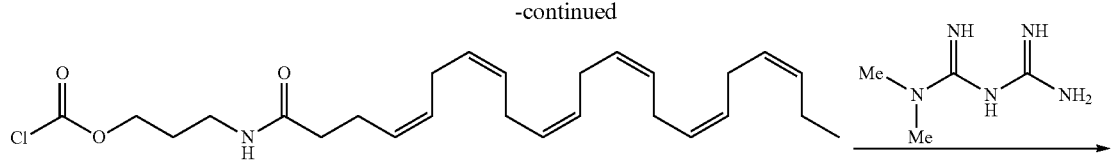

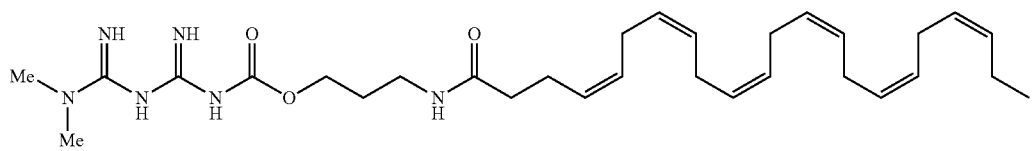

Compound I-3

To a solution of (4Z,7Z,10Z,13Z,16Z,19Z)-docosa-4,7,10,13,16,19-hexaenoic acid (3.3 g, 10 mmol) in 50 mL of anhydrous $CH_2Cl_2$ were added EDCI (2.2 g, 11.0 mmol), HOBt (1.5 g, 11.0 mmol), and $Et_3N$ at 0° C. The reaction mixture was allowed to warm to room temperature, and stirred overnight. The reaction mixture was diluted with 50 mL of $CH_2Cl_2$ and washed successively with water (3×20 mL), brine (30 mL). The resulting organic layer was dried over anhydrous $Na_2SO_4$ and then concentrated under reduced pressure. The residue was purified by column chromatography (gradient elution from 2:1 pentane/EtOAc to 1:2 pentane/EtOAc) to afford 3.0 g of (4Z,7Z,10Z,13Z,16Z,19Z)—N-(3-hydroxypropyl)docosa-4,7,10,13,16,19-hexaenamide (78% yield).

(4Z,7Z,10Z,13Z,16Z,19Z)—N-(3-Hydroxypropyl)docosa-4,7,10,13,16,19-hexaenamide (3.0 g, 7.8 mmol) was dissolved in 40 mL of $CH_2Cl_2$ and pyridine (650 mg, 8.2 mmol) was added. Triphosgene (7.8 mmol) was then added in portions at 0° C. over a period of 15 min. The resulting reaction mixture was stirred at 0° C. until the reaction was completed, as determined by TLC. The solids were removed by filtration and the filtrate was concentrated under reduced pressure. The resulting residue was purified by column chromatography to afford 1.5 g of 3-((4Z,7Z,10Z,13Z,16Z,19Z)-docosa-4,7,10,13,16,19-hexaenamido)propyl carbonochloridate. (43% yield).

The free base form of metformin was generated according to the procedures outlined in Huttunen et al *Synthesis* 2008, p. 3619-3624. To a suspension of this free base form of metformin (130 mg, 1.0 mmol) in $CH_2Cl_2$ was added a solution of 3-((4Z,7Z,10Z,13Z,16Z,19Z)-docosa-4,7,10,13,16,19-hexaenamido)propyl carbonochloridate (200 mg, 0.45 mmol) in 4 mL of anhydrous $CH_2Cl_2$ dropwise at 0° C. After 1 hour, LC-MS showed the reaction was completed. The reaction mixture was filtered and the filtrate was concentrated under reduced pressure. The resulting residue was re-dissolved with 2 mL of MeOH, and purified by preparative HPLC using a mixture of aqueous acetonitrile that has been buffered with 0.1% TFA to afford 65 mg of compound I-3 (12% yield). MS (EI) calcd for $C_{30}H_{48}N_6O_3$: 540.38. Found: 541 $[M+H]^+$ $^1H$ NMR (400 MHz, $CDCl_3$) δ 7.62 (br, 3H), 6.80 (br, 1H), 3.38-5.28 (m, 12H), 4.17 (br, 2H), 3.28 (br, 2H), 3.02 (s, 6H), 2.94-2.81 (m, 10H), 2.36 (br, 2H), 2.24 (br, 2H), 2.11-2.02 (m, 2H), 1.83 (br, 2H), 0.97 (t, J=7.2 Hz, 3H).

Example 6

Preparation of Compound I-4

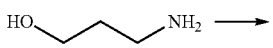

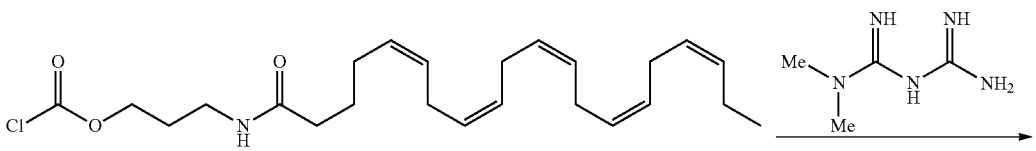

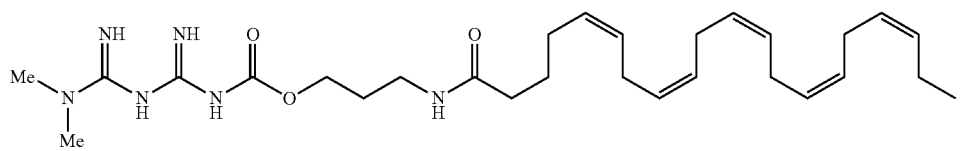

Compound I-4

The same experimental procedure outlined in example 5 was used, substituting (5Z,8Z,11Z,14Z,17Z)-eicosa-5,8,11,14,17-pentaenoic acid for (4Z,7Z,10Z,13Z,16Z,19Z)-docosa-4,7,10,13,16,19-hexaenoic acid. MS (EI) calcd for $C_{28}H_{46}N_6O_3$ 514.36. found 515 $[M+H]^+$.

Example 7

Preparation of Compound I-1

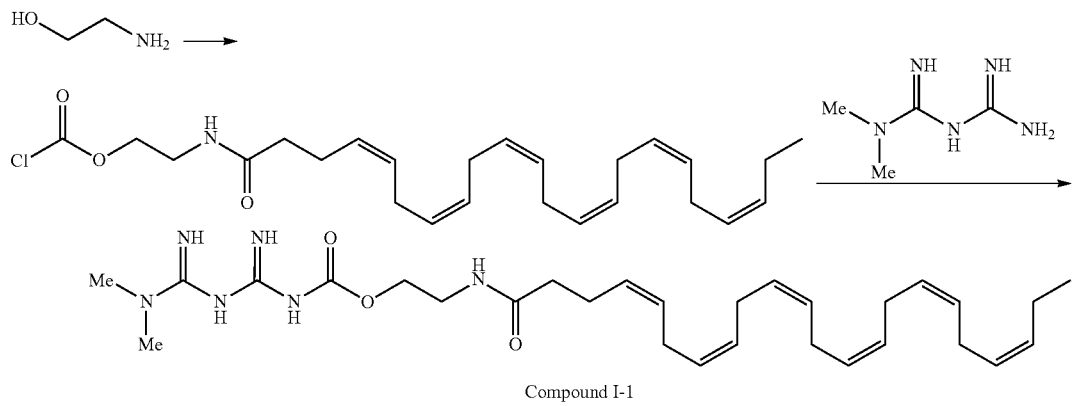

The same experimental procedure outlined in example 5 was used, substituting 2-aminoethanol for 3-aminopropanol. MS (EI) calcd for $C_{29}H_{46}N_6O_3$ 526.36. found 527 [M+H]$^+$.

Example 8

Preparation of Compound I-28

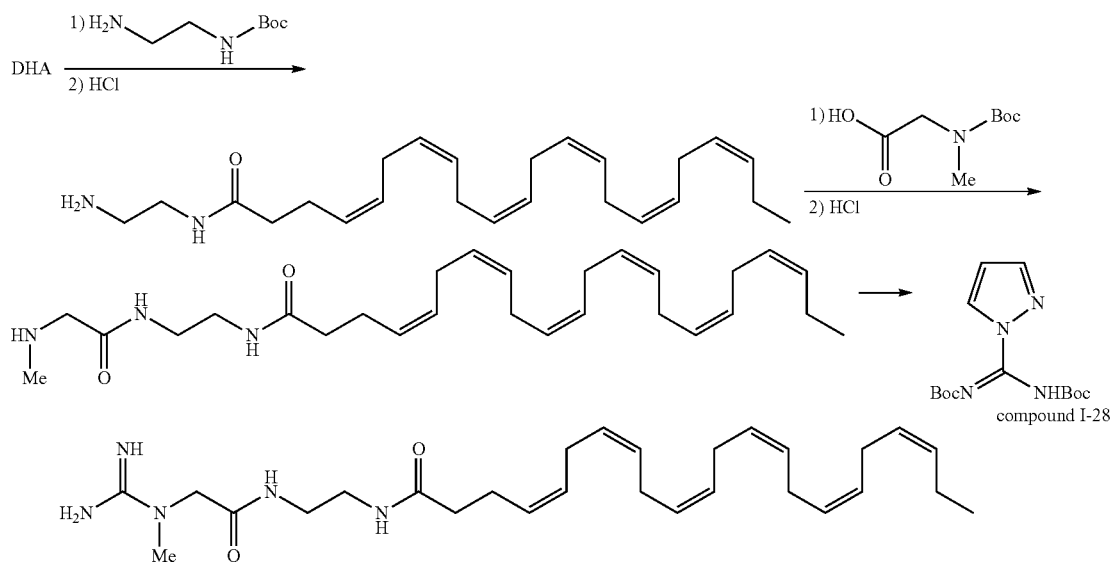

(4Z,7Z,10Z,13Z,16Z,19Z)-docosa-4,7,10,13,16,19-hexaenoic acid (1 mmol) was taken up in CH$_3$CN (5 mL) along with tert-butyl 2-aminoethylcarbamate (1 mmol) and EDCI (1.1 mmol). The resulting reaction mixture was stirred at room temperature for 2 h. It was then washed with brine, dried over Na$_2$SO$_4$, filtered and concentrated under reduced pressure. Purification by silica gel chromatography (CH$_2$Cl$_2$) afforded tert-butyl 2-(4Z,7Z,10Z,13Z,16Z,19Z)-docosa-4,7,10,13,16,19-hexaenamidoethylcarbamate.

tert-Butyl 2-(4Z,7Z,10Z,13Z,16Z,19Z)-docosa-4,7,10,13,16,19-hexaenamidoethylcarbamate (600 mg, 1.27 mmol) was taken up in 2 mL of EtOAc along with 2 mL of saturated HCl in EtOAc at 0° C. The resulting reaction mixture was stirred at room temperature for 2 h. Saturated aqueous Na$_2$CO$_3$ was added to adjust the pH=8. The organic layer was separated, dried (Na$_2$SO$_4$) and concentrated under reduced pressure to afford 470 mg of the (4Z,7Z,10Z,13Z,16Z,19Z)—N-(2-aminoethyl)docosa-4,7,10,13,16,19-hexaenamide (98% yield).

2-((tert-Butoxycarbonyl)(methyl)amino)acetic acid (240 mg, 1.27 mmol) was taken up in 5 mL of CH$_2$Cl$_2$ along with (4Z,7Z,10Z,13Z,16Z,19Z)—N-(2-aminoethyl)docosa-4,7,10,13,16,19-hexaenamide (470 mg, 1.27 mmol), HATU (724 mg, 1.27 mmol). The resulting reaction mixture was stirred at room temperature for 20 h. The organic layer was washed with saturated NH$_4$Cl, brine, dried (Na$_2$SO$_4$) and concentrated under reduced pressure. The resulting residue was purified by silica gel chromatography to afford 650 mg of tert-butyl (2-((2-((4Z,7Z,10Z,13Z,16Z,19Z)-docosa-4,7,10,13,16,19-hexaenamido)ethyl)amino)-2-oxoethyl)(methyl)carbamate (56% yield).

tert-Butyl (2-((2-((4Z,7Z,10Z,13Z,16Z,19Z)-docosa-4,7,10,13,16,19-hexaenamido)ethyl)amino)-2-oxoethyl)(methyl)carbamate was taken up in 2 mL of EtOAc and 2 mL of saturated HCl in EtOAc was added. The resulting reaction mixture was stirred at room temperature for 2 h. Enough saturated aqueous Na$_2$CO$_3$ was added to adjust the pH=8. The aqueous layer was extracted with EtOAc. The combined organic layers were washed with brine, dried (Na$_2$SO$_4$) and concentrated under reduced pressure to afford 530 mg of (4Z,7Z,10Z,13Z,16Z,19Z)—N-(2-(2-(methylamino)acetamido)ethyl)docosa-4,7,10,13,16,19-hexaenamide (99% yield).

(4Z,7Z,10Z,13Z,16Z,19Z)—N-(2-(2-(Methylamino)acetamido)ethyl)docosa-4,7,10,13,16,19-hexaenamide (416 mg, 1.2 mmol) was taken up in 10 mL of DMF along with tert-butyl (((tert-butoxycarbonyl)amino)(1H-pyrazol-1-yl)methylene)carbamate (154 mg, 1.2 mmol) and DIEA (154 mg, 1.2 mmol). The resulting reaction mixture was stirred at room temperature for 24 h. It was then diluted with EtOAc and washed with water. The organic layer was washed with brine, dried (Na$_2$SO$_4$) and concentrated under reduced pressure. Purification by silica gel chromatography (pentane/EtOAc) afforded 350 mg of the di-Boc derivative of (4Z,7Z,10Z,13Z,16Z,19Z)—N-(2-(2-(1-methylguanidino)acetamido)ethyl)docosa-4,7,10,13,16,19-hexaenamide (43% yield). MS (EI) calcd for C$_{32}$H$_{51}$N$_3$O$_4$ 541.39. found 542 [M+H]$^+$.

The di-Boc derivative of (4Z,7Z,10Z,13Z,16Z,19Z)—N-(2-(2-(1-methylguanidino)acetamido)ethyl)docosa-4,7,10,13,16,19-hexaenamide (350 mg, 0.516 mmol) was taken up in 2 mL of EtOAc and 2 mL of saturated HCl in EtOAc was added. The resulting reaction mixture was stirred at room temperature for 2 h. Enough saturated aqueous Na$_2$CO$_3$ was added to adjust the pH=8. The organic layer was separated, dried (Na$_2$SO$_4$) concentrated under reduced pressure. The resulting residue was purified by silica gel chromatography (95% CH$_2$Cl$_2$, 5% MeOH) to afford 140 mg of compound I-28, namely (4Z,7Z,10Z,13Z,16Z,19Z)—N-(2-(2-(1-methylguanidino)acetamido)ethyl)docosa-4,7,10,13,16,19-hexaenamide. MS (EI) calcd for C$_{28}$H$_{45}$N$_5$O$_2$ 483.36. found 484 [M+H]$^+$.

$^1$H NMR (400 MHz, DMSO) δ 0.92 (t, J=7.6 Hz, 3H), 1.50-1.53 (m, 2H), 2.02-2.06 (m, 6H), 2.78-2.82 (m, 9H), 2.90 (s, 3H), 3.11-3.13 (m, 7H), 5.29-5.37 (m, 12H), 7.39 (br, 3H), 7.60 (br, 1H), 7.95 (br, 1H).

Example 9

Preparation of Compound I-31

The same procedure outlined in example 8 was used, substituting tert-butyl 2-((2-aminoethyl)(methyl)amino)ethylcarbamate for tert-butyl 2-aminoethylcarbamate. tert-Butyl 2-((2-aminoethyl)(methyl)amino)ethylcarbamate, in turn, could be prepared as follows: N1-(2-aminoethyl)-N1-methylethane-1,2-diamine (5.0 g, 42.7 mmol) was dissolved in 100 mL of CH$_2$Cl$_2$ and cooled to 0° C. A solution of di-tert-butylcarbonate (0.93 g, 4.27 mmol) in CH$_2$Cl$_2$ (10 mL) was then added dropwise at 0° C. over a period of 15 min. The resulting reaction mixture was stirred at 0° C. for 30 min and then warmed to room temperature. After stirring at room temperature for 2 h, the reaction mixture was diluted with CH$_2$Cl$_2$ (100 mL). The organic layer was washed with brine (3×25 mL), dried (Na$_2$SO$_4$) and concentrated under reduced pressure to afford 1.1 g of tert-butyl 2-((2-aminoethyl)(methyl)amino)ethylcarbamate. Compound I-31: MS (EI) calcd for C$_{31}$H$_{52}$N$_6$O$_2$ 540.42. found 541 [M+H]$^+$.

Example 10

Preparation of Compound I-32

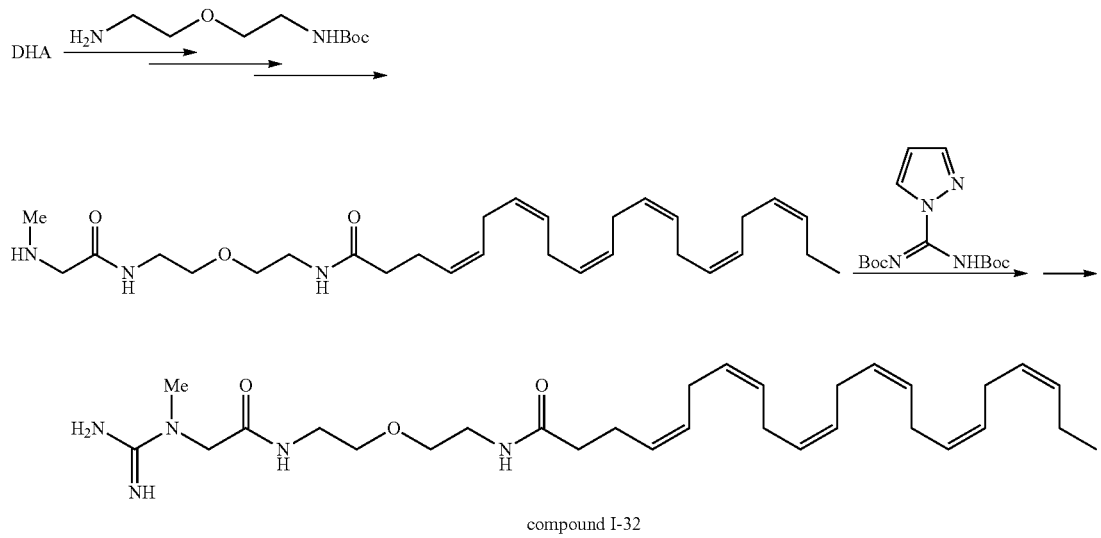

compound I-32

The same procedure outlined in example 8 was used, substituting tert-butyl (2-(2-aminoethoxy)ethyl)carbamate for tert-butyl 2-aminoethylcarbamate. tert-Butyl (2-(2-aminoethoxy)ethyl)carbamate, in turn, could be prepared as follows: Sodium hydroxide (400 mg, 10 mmol) was dissolved in 70 mL of MeOH and 2-(2-aminoethoxy)ethanamine dihydrochloride (1.0 g, 5.65 mmol) was added. The resulting reaction mixture was stirred at room temperature for 30 min. A solution containing Boc$_2$O (740 mg, 3.40 mmol) in 15 mL of THF was then added dropwise, at room temperature, over a period of 15 min. The resulting reaction mixture was stirred at room temperature for 18 h, then concentrated under reduced pressure. The resulting residue was taken up in 200 mL of CH$_2$Cl$_2$ and stirred vigorously at room temperature for 4 h. The mixture was filtered and the filtrate was concentrated under reduced pressure to afford 850 mg of tert-butyl 2-(2-aminoethoxy)ethylcarbamate (74% yield). Compound I-32: MS (EI) calcd for C$_{30}$H$_{49}$N$_5$O$_3$ 527.38. found 528 [M+H]$^+$.

Example 11

Preparation of Compound I-19

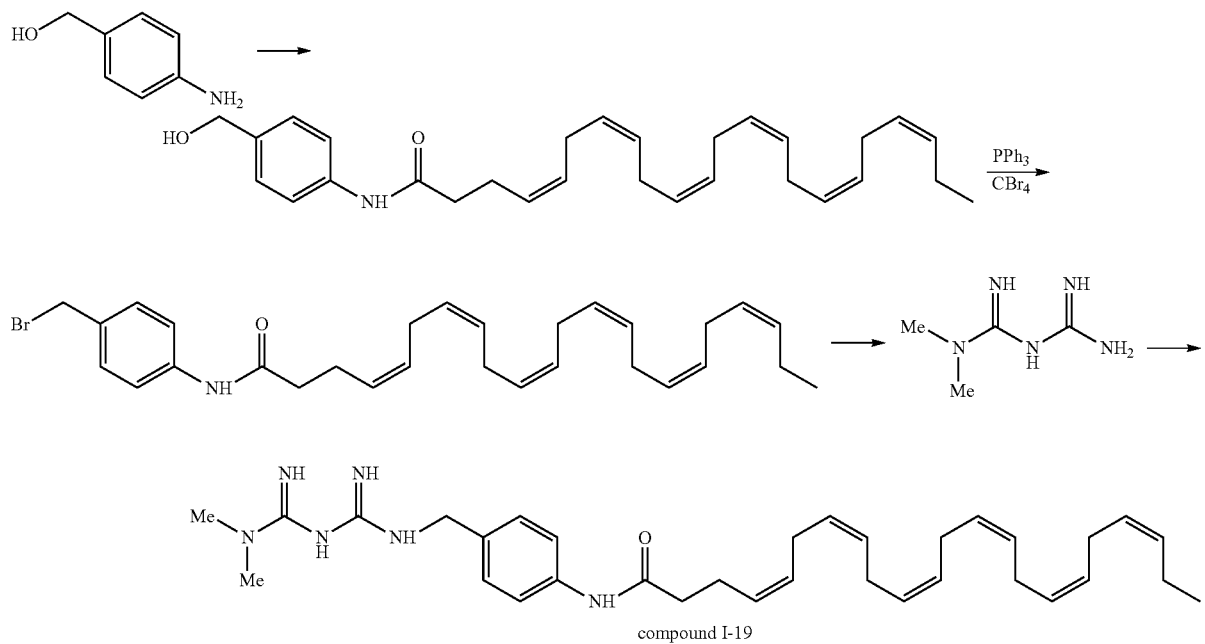

compound I-19

(4-Aminophenyl)methanol (1 mmol) was taken up in 15 mL of $CH_2Cl_2$ along with (4Z,7Z,10Z,13Z,16Z,19Z)-docosa-4,7,10,13,16,19-hexaenoic acid (1 mmol) and HATU (1.1 mmol). The resulting reaction mixture was stirred at room temperature for 6 h and diluted with saturated aqueous $NH_4Cl$. The two layers were separated and the organic layer was washed with brine, dried ($Na_2SO_4$) and concentrated under reduced pressure. Purification by silica gel chromatography (95% $CH_2Cl_2$, 5% MeOH) afforded (4Z,7Z,10Z,13Z,16Z,19Z)—N-(4-(hydroxymethyl)phenyl)docosa-4,7,10,13,16,19-hexaenamide.

(4Z,7Z,10Z,13Z,16Z,19Z)—N-(4-(hydroxymethyl)phenyl)docosa-4,7,10,13,16,19-hexaenamide (0.5 mmol) was taken up in 5 mL of $CH_2Cl_2$ and cooled to 0° C. Triphenylphosphine (0.5 mmol) and carbon tetrabromide (0.5 mmol) were added and the resulting reaction mixture was slowly warmed to room temperature. After 2 h at room temperature, the reaction mixture was concentrated under reduced pressure. The resulting residue can be purified by silica gel chromatography to afford (4Z,7Z,10Z,13Z,16Z,19Z)—N-(4-(bromomethyl)phenyl)docosa-4,7,10,13,16,19-hexaenamide.

(4Z,7Z,10Z,13Z,16Z,19Z)—N-(4-(Bromomethyl)phenyl)docosa-4,7,10,13,16,19-hexaenamide (0.5 mmol) and the free base of metformin (0.5 mmol) were taken up in $CH_2C_2$ (5 mL) and stirred at room temperature for 2 h. The reaction mixture was then concentrated under reduced pressure. The resulting residue was purified by preparative HPLC using a mixture of aqueous $CH_3CN$ that has been buffered with 0.1% TFA to afford compound I-19. Compound I-19: MS (EI) calcd for $C_{33}H_{48}N_6O$ 544.39. found 545 $[M+H]^+$.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

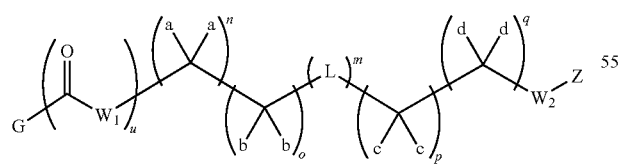

Formula I or a pharmaceutically acceptable salt, enantiomer or stereoisomer thereof;
wherein
$W_1$ and $W_2$ are each independently O, S, NH, or NR, or $W_1$ and $W_2$ can be taken together to form an imidazolidine or piperazine group;
G is independently

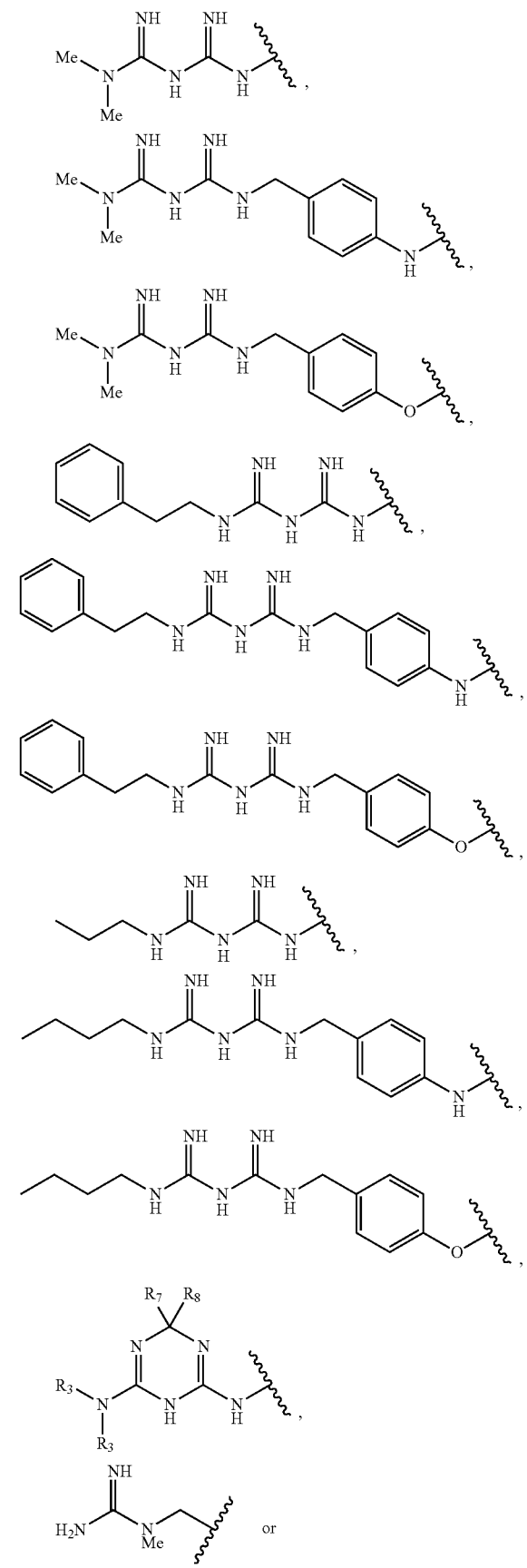

-continued

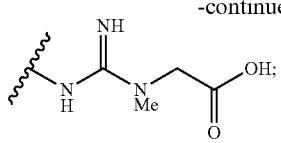

each a, b, c, and d is independently —H, -D, —CH₃, —OCH₃, —OCH₂CH₃, —C(O)OR, —O—Z, or benzyl, or two of a, b, c, and d can be taken together, along with the single carbon to which they are bound, to form a cycloalkyl or heterocycle;

each n, o, p, and q is independently 0, 1 or 2;

L is null;

$R_7$ and $R_8$ are independently H, $C_1$-$C_6$ alkyl, trifluoromethyl, a cycloalkyl, a heterocycle, or $R_7$ and $R_8$ can be taken together to form a 3-8 membered ring that can optionally contain one or more heteroatoms chosen from N, O, and S;

m is 0;

u is 1;

each $R_3$ is independently H or $C_1$-$C_6$ alkyl and in $NR_3R_3$, both $R_3$ when taken together with the nitrogen to which they are attached can form a heterocyclic ring selected from the group consisting of pyrrolidine, piperidine, morpholine, piperazine, and pyrrole;

each Z is independently —H,

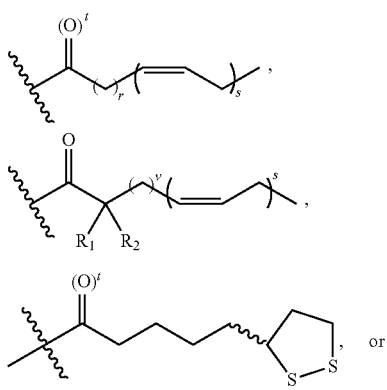

with the proviso that there is at least one of

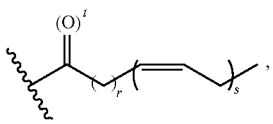

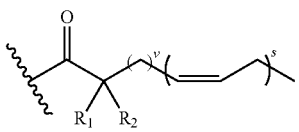

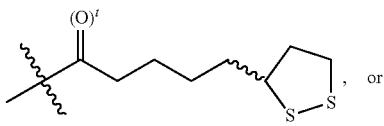

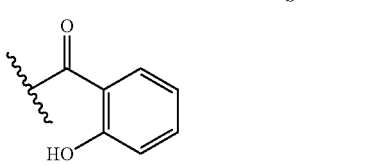

in the compound;

each r is independently 2, 3, or 7;

each s is independently 3, 5, or 6;

each t is independently 0 or 1;

each v is independently 1, 2, or 6;

$R_1$ and $R_2$ are independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —NH₂, —NH($C_1$-$C_3$ alkyl), —N($C_1$-$C_3$ alkyl)₂, —NH(C(O)$C_1$-$C_3$ alkyl), —N(C(O)$C_1$-$C_3$ alkyl)₂, —SH, —S($C_1$-$C_3$ alkyl), —S(O)$C_1$-$C_3$ alkyl, or —S(O)₂ $C_1$-$C_3$ alkyl; and each R is independently —H, —$C_1$-$C_3$ alkyl, or straight or branched $C_1$-$C_4$ alkyl optionally substituted with OH or halogen.

2. A compound of the Formula Ia:

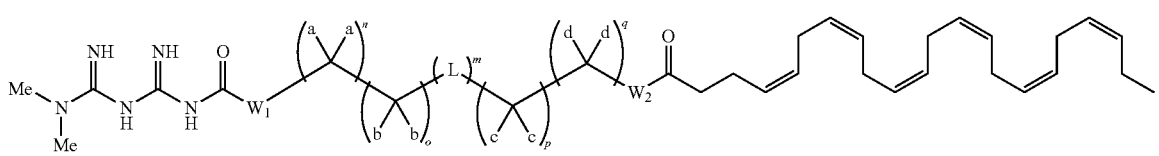

Formula Ia or a pharmaceutically acceptable salt, enantiomer or stereoisomer thereof;

wherein $W_1$ and $W_2$ are each independently O, S, NH, or NR, or $W_1$ and $W_2$ can be taken together to form an imidazolidine or piperazine group;

each a, b, c, and d is independently —H, -D, —CH₃, —OCH₃, —OCH₂CH₃, —C(O)OR, or benzyl, or two of

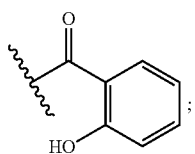

a, b, c, and d can be taken together, along with the single carbon to which they are bound, to form a cycloalkyl or heterocycle;

each n, o, p, and q is independently 0, 1 or 2;

L is null;

m is 0; and each R is independently —H, —$C_1$-$C_3$ alkyl, or straight or branched $C_1$-$C_4$ alkyl optionally substituted with OH or halogen.

3. A compound of the Formula Ib:

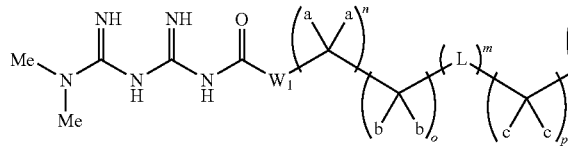

Formula Ib or a pharmaceutically acceptable salt, enantiomer or stereoisomer thereof;

wherein $W_1$ and $W_2$ are each independently O, S, NH, or NR, or $W_1$ and $W_2$ can be taken together to form an imidazolidine or piperazine group;

each a, b, c, and d is independently —H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0, 1 or 2;

L is null;

m is 0; and each R is independently —H, —$C_1$-$C_3$ alkyl, or straight or branched $C_1$-$C_4$ alkyl optionally substituted with OH or halogen.

4. A compound of the Formula Ic:

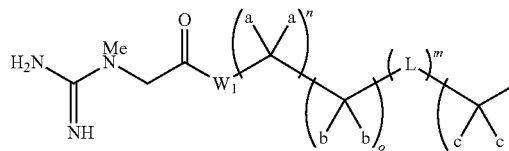

Formula Ic or a pharmaceutically acceptable salt, enantiomer or stereoisomer thereof;

wherein $W_1$ and $W_2$ are each independently O, S, NH, or NR, or $W_1$ and $W_2$ can be taken together to form an imidazolidine or piperazine group;

each a, b, c, and d is independently —H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0, 1 or 2;

L is null;

m is 0; and each R is independently —H, —$C_1$-$C_3$ alkyl, or straight or branched $C_1$-$C_4$ alkyl optionally substituted with OH or halogen.

5. A compound of the Formula Id:

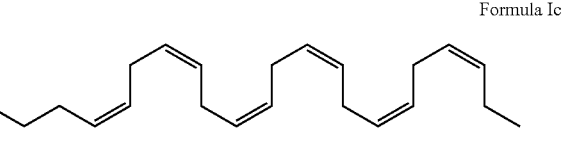

Formula Id or a pharmaceutically acceptable salt, enantiomer or stereoisomer thereof;

wherein $W_1$ and $W_2$ are each independently O, S, NH, or NR, or $W_1$ and $W_2$ can be taken together to form an imidazolidine or piperazine group;

each a, b, c, and d is independently —H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0, 1 or 2;

L is null;

m is 0; and each R is independently —H, —$C_1$-$C_3$ alkyl, or straight or branched $C_1$-$C_4$ alkyl optionally substituted with OH or halogen.
6. The compound of claim 2, wherein the compound is selected from the group consisting of
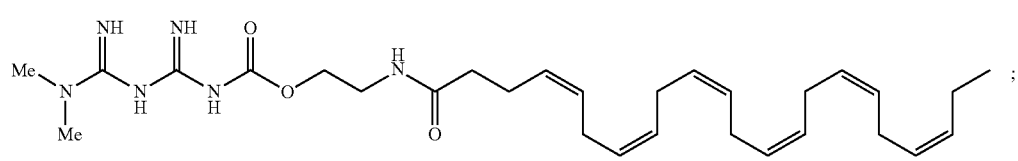
I-1
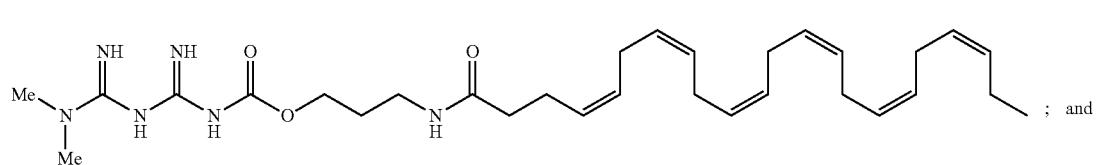
I-3
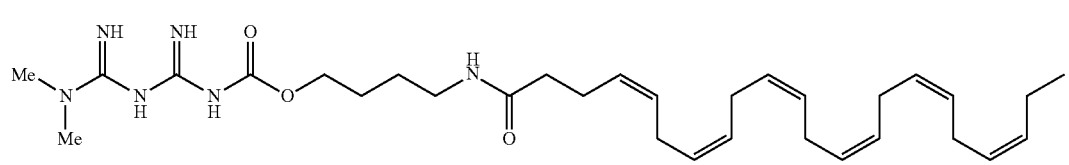
I-5
7. The compound of claim 3, wherein the compound is selected from the group consisting of
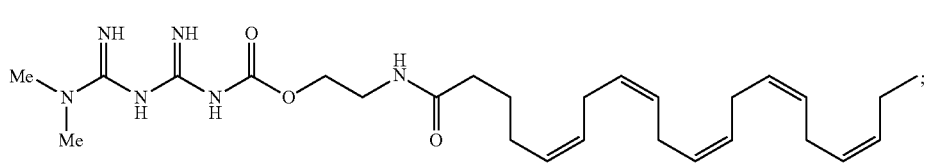
I-2
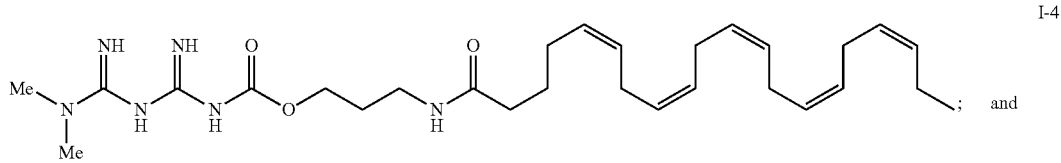
I-4
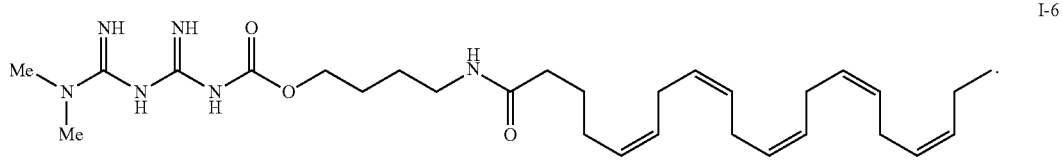
I-6
8. The compound of claim 4, wherein the compound is
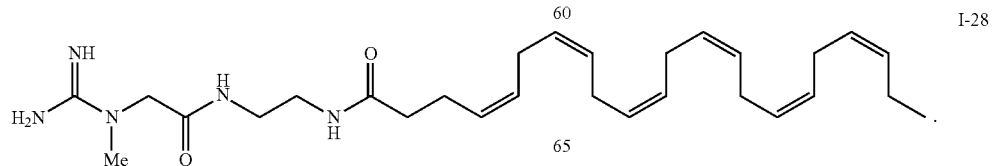
I-28

9. The compound of claim 5, wherein the compound is

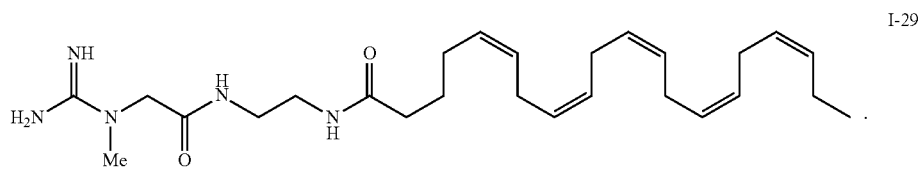 [SMILES: CC/C=C\C/C=C\C/C=C\C/C=C\C/C=C\CCCC(=O)NCCNC(=O)CN(C)C(=N)N]

I-29

10. A pharmaceutical composition comprising a compound of claim 1 and a pharmaceutically acceptable carrier.
11. A pharmaceutical composition comprising a compound of claim 2 and a pharmaceutically acceptable carrier.
12. A pharmaceutical composition comprising a compound of claim 3 and a pharmaceutically acceptable carrier.
13. A pharmaceutical composition comprising a compound of claim 4 and a pharmaceutically acceptable carrier.
14. A pharmaceutical composition comprising a compound of claim 5 and a pharmaceutically acceptable carrier.
15. A pharmaceutical composition comprising a compound of claim 6 and a pharmaceutically acceptable carrier.
16. A pharmaceutical composition comprising a compound of claim 7 and a pharmaceutically acceptable carrier.
17. A pharmaceutical composition comprising the compound of claim 8 and a pharmaceutically acceptable carrier.
18. A pharmaceutical composition comprising the compound of claim 9 and a pharmaceutically acceptable carrier.

* * * * *